(12) United States Patent
Traverso et al.

(10) Patent No.: US 10,814,115 B2
(45) Date of Patent: Oct. 27, 2020

(54) MICRONEEDLE DEVICES AND USES THEREOF

(71) Applicants: MASSACHUSETTS INSTITUTE OF TECHNOLOGY, Cambridge, MA (US); THE GENERAL HOSPITAL CORPORATION, Boston, MA (US)

(72) Inventors: Carlo Giovanni Traverso, Cambridge, MA (US); Avraham D. Schroeder, Newton, MA (US); Baris Erinc Polat, Brighton, MA (US); Carl Magnus Schoellhammer, Santa Monica, CA (US); Daniel Blankschtein, Brookline, MA (US); Daniel G. Anderson, Sudbury, MA (US); Robert S. Langer, Newton, MA (US)

(73) Assignees: MASSACHUSETTS INSTITUTE OF TECHNOLOGY, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 578 days.

(21) Appl. No.: 13/728,300

(22) Filed: Dec. 27, 2012

(65) Prior Publication Data
US 2013/0165772 A1 Jun. 27, 2013

Related U.S. Application Data

(60) Provisional application No. 61/580,648, filed on Dec. 27, 2011.

(51) Int. Cl.
*A61M 37/00* (2006.01)
*A61M 31/00* (2006.01)
*A61M 5/00* (2006.01)

(52) U.S. Cl.
CPC ........ *A61M 37/0015* (2013.01); *A61M 5/007* (2013.01); *A61M 31/002* (2013.01); *A61M 2037/0023* (2013.01)

(58) Field of Classification Search
CPC ........ A61M 2037/0023; A61M 31/002; A61M 37/0015; A61M 2037/0061; A61M 2037/003
See application file for complete search history.

(56) References Cited

U.S. PATENT DOCUMENTS 6,611,707 B1 * 8/2003 Prausnitz ............. A61B 5/1411
                                                   604/21
7,547,294 B2 6/2009 Seward et al.
(Continued)

OTHER PUBLICATIONS

International Search Report of PCT/US12/71778, dated Apr. 24, 2013, 5 pages.
(Continued)

*Primary Examiner* — Rebecca E Eisenberg
*Assistant Examiner* — Weng Lee
(74) *Attorney, Agent, or Firm* — Choate, Hall & Stewart LLP; Brenda Herschbach Jarrell; Dana M. Daukss

(57) ABSTRACT

The present disclosure provides devices and uses thereof. A devices disclosed herein comprises a plurality of microneedles adapted to protrude from the device. In some embodiments, a device is dimensioned and constructed to carry a payload, so that the payload can be delivered to an internal tissue of a subject or through a wall of a vessel after interaction with microneedles. In some embodiments, devices can be used for oral or intravenous administration. In some embodiments, devices can be used for implantation such as vaginal, rectal, urethral or bladder suppository or pessary.

22 Claims, 24 Drawing Sheets

(56) References Cited

U.S. PATENT DOCUMENTS

| | | |
|---|---|---|
| 7,918,814 B2 | 4/2011 | Prausnitz et al. |
| 2002/0082543 A1* | 6/2002 | Park .................. A61B 5/1411 604/21 |
| 2003/0153900 A1* | 8/2003 | Aceti .................. A61B 5/1411 604/890.1 |
| 2004/0106904 A1* | 6/2004 | Gonnelli ............. A61B 17/205 604/173 |
| 2005/0261632 A1* | 11/2005 | Xu ..................... A61K 9/0021 604/173 |
| 2006/0062852 A1* | 3/2006 | Holmes ............... A61B 5/0024 424/484 |
| 2007/0038181 A1* | 2/2007 | Melamud .......... A61B 17/3478 604/158 |
| 2008/0146489 A1 | 6/2008 | Pacetti et al. |
| 2008/0208076 A1* | 8/2008 | Cho ................. A61B 10/0233 600/562 |
| 2008/0213461 A1* | 9/2008 | Gill .................... A61K 9/0021 427/2.3 |
| 2008/0311177 A1 | 12/2008 | Hammond et al. |
| 2011/0087195 A1* | 4/2011 | Uhland ............ A61M 37/0015 604/515 |
| 2011/0160699 A1* | 6/2011 | Imran ................ A61K 31/155 604/514 |

OTHER PUBLICATIONS

Written Opinion of PCT/US12/71778, dated Apr. 24, 2013, 6 pages.

Aggarwal, S., What's fueling the biotech engine—2009-2010, Nat. Biotechnol., 28(11):1165-71 (2010).

Anal, A.K., Stimuli-induced Pulsatile or Triggered Release Delivery Systems for Bioactive Compounds, Recent Patents on Endocrine, Metabolic & Immune Drug Discovery, 1:83-90 (2007).

* cited by examiner

MICRONEEDLE DEVICES AND USES THEREOF

CROSS-REFERENCE TO RELATED APPLICATION

This application claims priority to and the benefit of, and incorporates herein by reference in its entirety, U.S. Provisional Patent Application No. 61/580,648, filed Dec. 27, 2011.

BACKGROUND

An active agent or drug may be administered to a patient through various means. For example, a drug may be ingested, inhaled, injected, delivered intravenously, etc. In some applications, a drug may be administered transdermally. In some transdermal applications, such as transdermal nicotine or birth control patches, a drug is absorbed through the skin.

Although transdermal drug delivery offers certain advantages over conventional oral administration, it would be beneficial to promote innovations suitable for use via the oral route. More generally, there remains a need for devices and methods that enable enhanced drug delivery, in particular, when administered or implanted internally in patients.

SUMMARY

The present disclosure provides a microneedle device and uses thereof. Such a device comprises a plurality of microneedles adapted to protrude from the device. In some embodiments, a device is dimensioned and constructed to carry a payload, so that the payload can be delivered to an internal tissue of a subject or through a wall of a vessel after interaction with microneedles.

A device described herein can be used in various medical applications. In some embodiments, devices can be administered to or implanted in an internal tissue, for example that is part of an organ, for example an internal organ (e.g., a viscus). In some embodiments, a provided device can be administered orally, intravenously, or sublingually; vaginally, rectally, urethrally or as a bladder suppository or pessary.

The present invention, among other things, encompasses the insight that the gastrointestinal (GI) tract and other body lumens/vessels is surprisingly tolerant of sharp objects, such that improved drug delivery can be achieved through administration/implantation of devices that include one or more protruding microneedles.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biologics": The term "biologics", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biologics include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biodegradable": As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

"Interaction": As used herein, the term "interaction", as used herein, refers to juxtaposition of surface area of two or more entities. In particular, in the present disclosure, the term is used to refer to juxtaposition of a device with a tissue of a subject. In some embodiments, the tissue is an internal tissue. As described herein, the present invention provides devices dimensioned for administration to or implantation in a subject (e.g., an internal tissue of a subject), which devices comprise a plurality of microneedles adapted to protrude therefrom, which device is arranged and constructed so that the microneedles, when protruding, interact with a subject's tissue (e.g., a subject's internal tissue). Such interaction is typically a non-covalent interaction, resulting from physical contact between the microneedles' surface and the tissue. In some embodiments, the microneedles penetrate or abrade the tissue. In some embodiments, such penetration or abrasion is subclinical so that, for example, administration or implantation of the device, with protruding needles, to an internal tissue of a subject does not cause significant harm to the subject. In some such embodiments, absence of significant harm is assessed, for example, by absence of significant physical discomfort, evidence of significant physical damage, and/or evidence of inflammation. In some embodiments, eating and/or sleeping behavior can provide evidence of physical discomfort (e.g., absence of change in such behaviors provides evidence of lack of significant harm). In some embodiments, interaction between microneedles of a provided device and internal tissues of a subject results in retention of the device at a particular location in the subject, for example so that a device containing microneedles shows delayed transit across a tissue and/or through an organ as compared with an otherwise comparable or identical device lacking the microneedles. In some embodiments, interaction between microneedles of a provided device and internal tissues of a subject is assessed as an adhesive force between the two surfaces. In some embodiments, interaction between microneedles of a provided device and internal tissues of a subject is assessed or determined by evaluating performance or behavior of the device (e.g., as compared with an appropriate control device such as an otherwise comparable or identical device lacking the microneedles and/or as compared with a reference standard or historical record) in contact with a model organism or tissue.

"Internal tissue": As used herein, "internal tissue" refers to cells, tissue, or organs, including mucosal tissues, vascular tissues, lymphatic vessels, gastrointestinal (GI) tissue, and cell membranes internal to a subject. In some embodiments, the internal tissue is part of an organ. In some embodiments, the organ is a component of the gastrointestinal tract. In some embodiments, the internal tissue is within an organ selected from the esophagus, small intestine, large intestine, rectum, penis, vagina, pelvis, coccyx, ovaries, fallopian tube, uterus, clitoris, perineum, urinary tract, testicle, rectum, peritoneum, stomach, duodenum, intestine, colon, liver, spleen, pancreas, kidney, adrenal gland, appendix and gall bladder and combinations thereof. In some embodiments, the internal tissue is within an internal GI tract. In some embodiments, the internal tissue is within a brain, stomach, pancreas, or liver.

"Hydrolytically degradable": As used herein, "hydrolytically degradable" polymers are polymers that degrade fully in the sole presence of water. In preferred embodiments, the polymers and hydrolytic degradation byproducts are biocompatible. As used herein, the term "non-hydrolytically degradable" refers to polymers that do not fully degrade in the sole presence of water.

"Microneedle": As used herein, "microneedle" refers to a protrusion from the device surface as described in the present disclosure. Microneedles generally are shape objects and in theory can be of any shape or design. A microneedle may be conical, cylindrical, tubular, pyramid-shaped or a hook-shaped. A microneedle may be straight, curved, or semi hook-shaped. Without being bound to any particular theory, a curved microneedle can facilitate retention of a device disclosed herein at a target site. A microneedle may protrude at angle from a device surface, the microneedle having a base integrally connected to the surface, a tip distal to the base, and a body therebetween. A microneedle or a portion of a microneedle may be solid or hollow. A microneedle or a portion of a microneedle can be porous or non-porous. A microneedle or a portion of a microneedle may be degradable or non-degradable. A plurality of microneedles used in accordance with the present disclosure may include a mixture of different microneedles. For instance, microneedles of the plurality may include microneedles having various lengths, base portion materials, body portion diameters (i.e., gauge), tip portion shapes, spacing between microneedles, coatings, etc. In some embodiments, a microneedle has a length less than about 2 cm. In some embodiments, a microneedle has a gauge/an outer diameter within a range of about 10 μm and about 600 μm.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For example, the physiological pH can range from about 7.0 to about 7.4. In some embodiments, the physiological pH in GI tract can range from about 1 to 8.

"Protrusion angle": The term "protrusion angle" as used herein can refer to an angle relative to the tangent to a surface of a device described herein.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": The term "subject" as used herein can refer to any multicellular organism including, for example, a human, an animal (e.g., a mammal), a plant, an insect, etc. In many embodiments, the subject is a human or non-human animal. In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Therapeutic agent", "medication" or "drug": As used herein, the phrases "therapeutic agent", "medication", or "drug" may be used interchangeably. They refer to any agent that, when administered, has a therapeutic effect and/or elicits a desired biological and/or pharmacological effect.

"Treating:" As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered/implanted to a targeted site who does not exhibit signs of a disease and/or exhibits only early signs of the disease for the purpose of decreasing the risk of developing pathology associated with the disease.

BRIEF DESCRIPTION OF THE DRAWING

The drawing is for illustration purposes only, not for limitation.

DETAILED DESCRIPTION OF CERTAIN EMBODIMENTS

Figure 1:
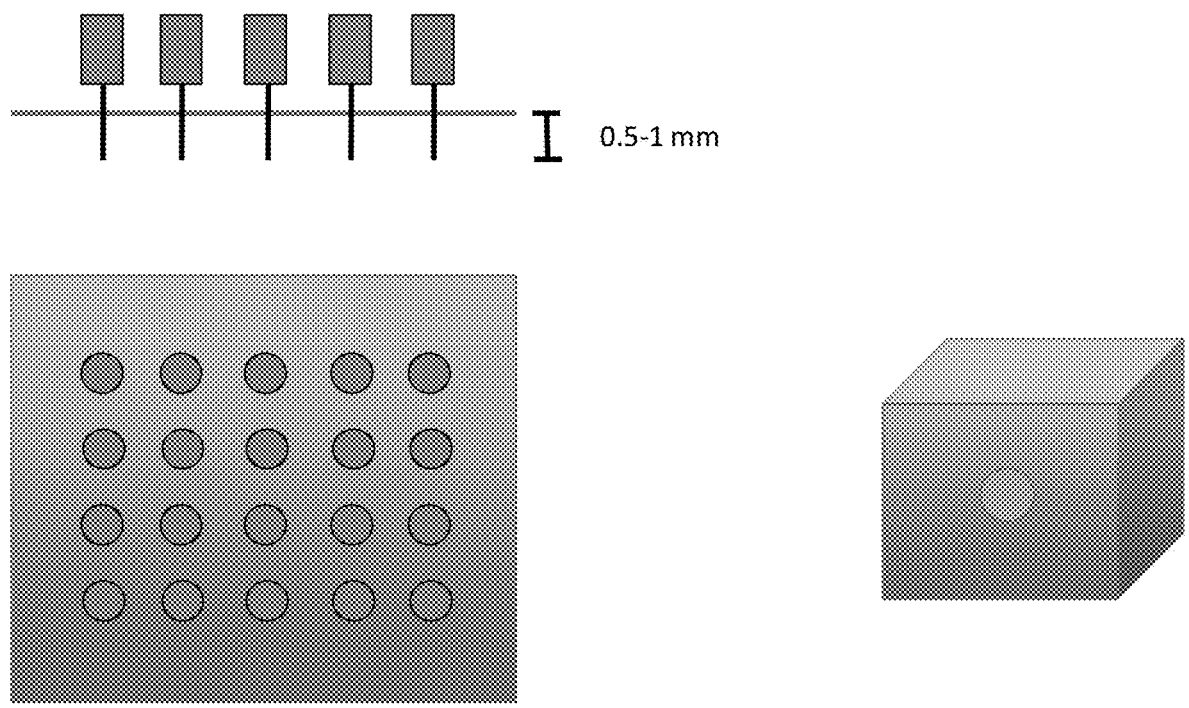
FIG. 1 depicts a schematic showing prototype 1 of a device according to the present application.
Figure 2:
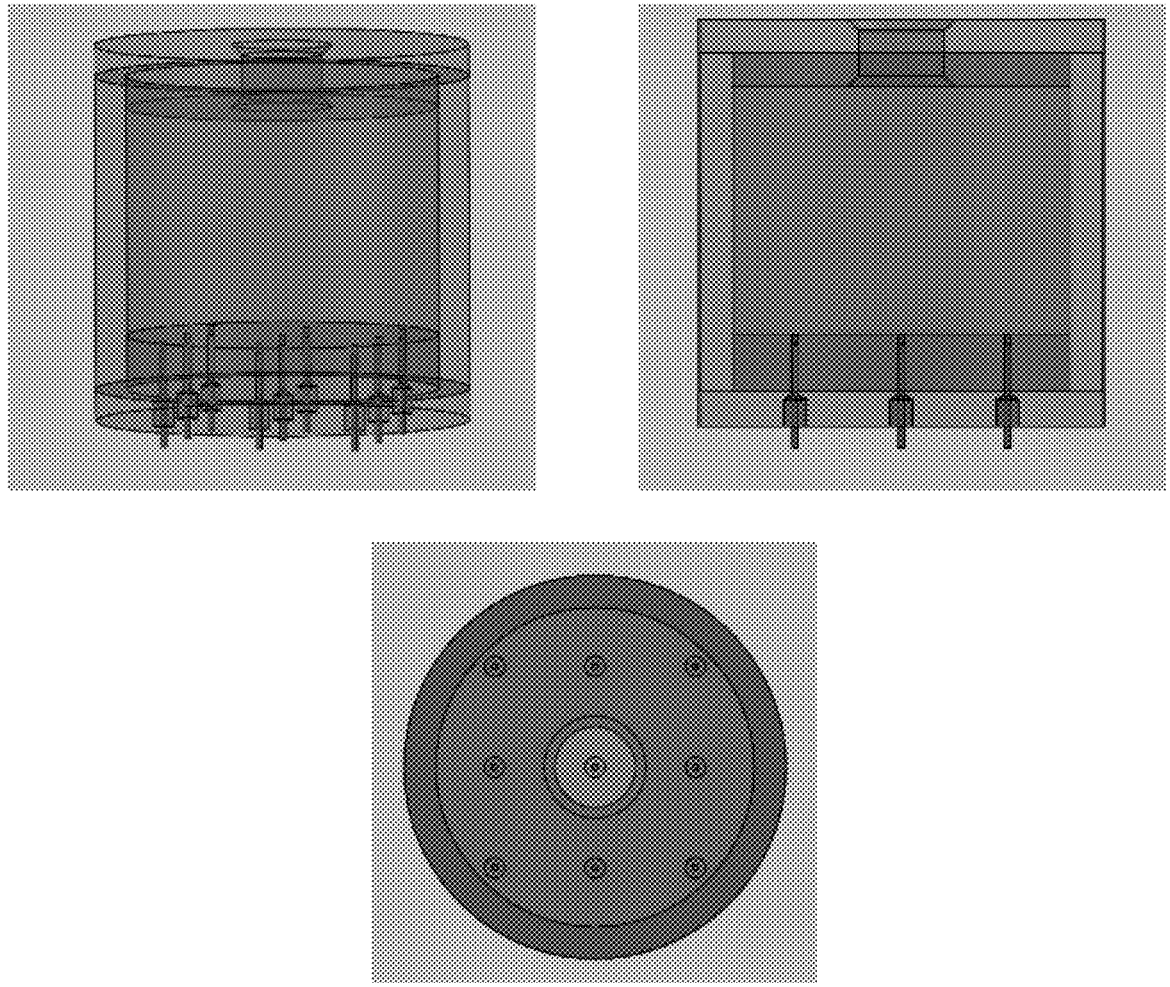
FIG. 2 illustrates technical drawings of prototype 1.

A device used in accordance with the present disclosure, in theory, can be of any shape or design. For example, a device or part of a device (e.g., a microneedle or the tip of a microneedle) can be or comprise a cube, a rectangle, a sphere, a cone, a pyramid, a cylinder, a tube, a ring, a tetrahedron, a hexagon, an octagon, or any irregular shapes. Exemplary device prototypes are illustrated in FIGS. 1-8.

In some embodiments, the greatest dimension or at least one dimension of a device may be about or less than about about 5 cm, about 4 cm, about 3 cm, about 2 cm, about 1 cm, about 5 mm, about 2 mm, about 1 mm, about 500 about 200 µm, about 100 about 50 about 20 about 10 about 5 about 1 about 500 nm, about 200 nm, about 100 nm, about 50 nm, about 20 nm, about 10 nm or even about 5 nm. In some embodiments, the greatest dimension or at least one dimension of a device may be more than about 1 nm, about 5 nm, about 10 nm, about 20 nm, about 50 nm, about 100 nm, about 200 nm, about 500 nm, about 1 about 5 about 10 about 20 about 50 µm, about 100 about 200 about 500 about 1 mm, about 2 mm, about 5 mm, about 1 cm, about 2 cm, about 3 cm, about 4 cm, or about 5 cm. In some embodiments, the greatest dimension or at least one dimension of a device may be within a range of about 0.1 microns to about 20 cm. In some embodiments, the greatest dimension or at least one dimension of a device may be within a range of about 1 micron to about 10 cm. In some embodiments, the greatest dimension or at least one dimension of a device may be within a range of about 1 cm to about 5 cm. In some embodiments, the greatest dimension or at least one dimension of a device may be within a range of about 0.1 µm to about 0.2 about 0.2 µm to about 0.5 about 1 µm to about 5 µm, about 5 µm to about 10 µm, about 10 µm to about 100 µm, about 100 µm to about 1 mm, about 1 mm to about 1 cm, about 1 cm to about 2 cm, about 2 cm to about 3 cm, about 3 cm to about 6 cm, or about 6 cm to about 10 cm. In some embodiments, the greatest dimension or at least one dimension of a device may be within a range of any two values above. In some embodiments, the dimensions of devices can be represented by a length, a width or a height in X, Y and Z axis where each dimension can be within a range of about 1 nm to about 10 cm.

An exemplary device suitable for use in accordance with the present disclosure is illustrated in FIGS. 4-7. A device may have an approximately column shape. Such a device may have a length of approximately 3 cm, with a cross section having a diameter of approximately 1 cm.

As for materials, a device including one or more microneedles protruding from the device surface as described herein can be made of or comprise one or more biocompatible materials. Exemplary materials include, but are not limited to, metals (e.g., gold, silver, platinum, steel or other alloys); metal-coated materials; metal oxides; plastics; ceramics; silicon; glasses; mica; graphite; hydrogels; and polymers such as non-degradable or biodegradable polymers; and combinations thereof. A device may comprise one or more materials. In general, materials can be utilized in any form (e.g., lyophilized or crystallized) and/or for different purposes (e.g., therapeutics, diagnostics, etc.)

In some embodiments, a device can be made of or comprise a magnetic material. For examples, a magnetic material can be utilized for positioning the device in a target site or orientation, to trigger delivery of a payload from the device, or to affect interaction of the microneedle to an internal tissue or a vessel wall.

In some embodiments, a device can be made of or comprise deformable materials (e.g., polymers). As an example, a device can be made of or comprise a deformable rubber so that the device swells enabling interaction of the microneedles protruding from the device surface to a tissue.

To give another example, a deformable device may be able to change size depending on pressure so that it can pass through lumens with diameters smaller than that of the device. Such a capability may be beneficial in a treating a patient with Crohn's disease where stricture may limit the passage of a rigid object and thereby cause obstruction whereas a deformable object may pass through.

In some embodiments, a device can be made of or comprise adhesive materials (e.g., adhesive polymers). As examples, bioadhesives such as chitosan and carbopol can be used. An adhesive material may be used to bring a device close to an internal tissue or a vessel wall facilitating the interaction of microneedles. Adhesiveness of the device can aid in fixing/implanting such a device at a target site for a prolonged period of time. For example, in treating an area of disease tissue, an adhesive device may act as a depot formulation for drugs used to treat chronic conditions. In addition or alternatively, adhesiveness may help slow down the transit of a device in a subject (e.g., a GI tract).

In some embodiments, a device can be made of or comprise one or more polymers. For example, a portion of the device (e.g., microneedles) and/or a coating as discussed below used in accordance with the present disclosure can be made of or comprise one or more polymers. Various polymers and methods known in the art can be used. Polymers may be natural polymers or unnatural (e.g. synthetic) polymers. In some embodiments, polymers can be linear or branched polymers. In some embodiments, polymers can be dendrimers. Polymers may be homopolymers or copolymers comprising two or more monomers. In terms of sequence, copolymers may be block copolymers, graft copolymers, random copolymers, blends, mixtures, and/or adducts of any of the foregoing and other polymers.

A polymer used in accordance with the present application can have a wide range of molecular weights. In some embodiments, the molecular weight of a polymer is greater than about 5 kDa. In some embodiments, the molecular weight of a polymer is greater than about 10 kDa. In some embodiments, the molecular weight of a polymer is greater than 50 kDa. In some embodiments, the molecular weight of a polymer is within a range of about 5 kDa to about 100 kDa. In some embodiments, the molecular weight of a polymer is within a range of about 10 kDa to about 50 kDa.

In some embodiments, polymers may be synthetic polymers, including, but not limited to, polyethylenes, polycarbonates (e.g. poly(1,3-dioxan-2-one)), polyanhydrides (e.g. poly(sebacic anhydride)), polyhydroxyacids (e.g. poly(β-hydroxyalkanoate)), polypropylfumarates, polycaprolactones, polyamides (e.g. polycaprolactam), polyacetals, polyethers, polyesters (e.g. polylactide, polyglycolide), poly (orthoesters), polycyanoacrylates, polyvinyl alcohols, polyurethanes, polyphosphazenes, polyacrylates, polymethacrylates, polyureas, polystyrenes, and polyamines and copolymers thereof. In some embodiments, polymers include polymers which have been approved for use in humans by the U.S. Food and Drug Administration (FDA) under 21 C.F.R. § 177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly(sebacic anhydride)); polyethers (e.g., polyethylene glycol); polyurethanes; polymethacrylates; polyacrylates; polycyanoacrylates; copolymers of PEG and poly(ethylene oxide) (PEO).

PEGs may be useful, in some embodiments, in accordance with the present application since they are nontoxic, non-immunogenic, inert to most biological molecules (e.g. proteins), and approved by the FDA for various clinical uses. PEG polymers can be covalently crosslinked using a variety of methods to form hydrogels. In some embodiments, PEG chains are crosslinked through photopolymerization using acrylate-terminated PEG monomers. In addition to chemical modification, block copolymers of PEG, such as triblock copolymers of PEO and poly(propylene oxide) (henceforth designated as PEO-b-PPO-b-PEO), degradable PEO, poly (lactic acid) (PLA), and other similar materials, can be used to add specific properties to the PEG.

In some embodiments, polymers used herein can be a degradable polymer. Such a degradable polymer can be hydrolytically degradable, biodegradable, thermally degradable, and/or photolytically degradable polyelectrolytes. For example, degradation of a device comprising a degradable polymer can be induced by the ingestion of a solution targeted to specifically degrade the device or a portion of the device (e.g., at least one microneedle).

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

Microneedles

In general, devices described herein comprises a plurality of microneedles. Microneedles are adapted (e.g., arranged and constructed) to protrude from the device surface so that after administration and/or implantation of the device, the microneedles penetrate and/or abrade an internal tissue of a subject or a wall of a vessel. In some embodiments, microneedles are incorporated into the device such that they adopt at least two different states with respect to the device body, their extent of protrusion differing in the at least two different states.

In certain embodiments, devices described herein may comprise a single microneedle.

In various embodiments, a plurality of microneedles includes two or more microneedles. For example, the number of microneedles can be on the order of a billion. In some embodiments, the number of microneedles may be within a range of about 2 to about 100, 000, about 100 to about 10,000, or about 500 to about 1,000. The number of microneedles, in certain embodiments, is within a range of 2-50, 50-500, 500-1,000, 1,000-5,000, 5,000-10,000, 10,000-50,000, 50,000-100,000.

In general, the number of microneedles utilized in a particular device may depend on the density and the area having microneedles protrude from. Theoretically, the density of microneedles can be as great as about 100 million/$cm^2$. For example, the density of microneedles may be about or greater than about 100,000/$cm^2$, about 10,000/$cm^2$, about 5,000/$cm^2$, about 1,000/$cm^2$, about 500/$cm^2$, about 100/$cm^2$, about 50/$cm^2$, about 10/$cm^2$, or even about 1/$cm^2$.

Figure 3:
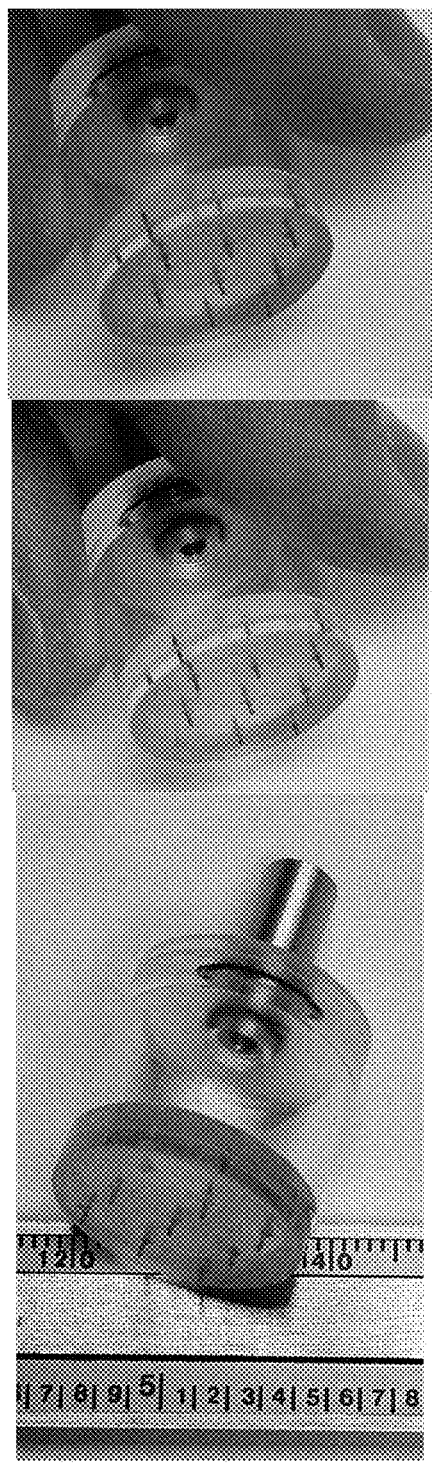
FIG. 3 shows photographs of prototype 1.
Figure 4:
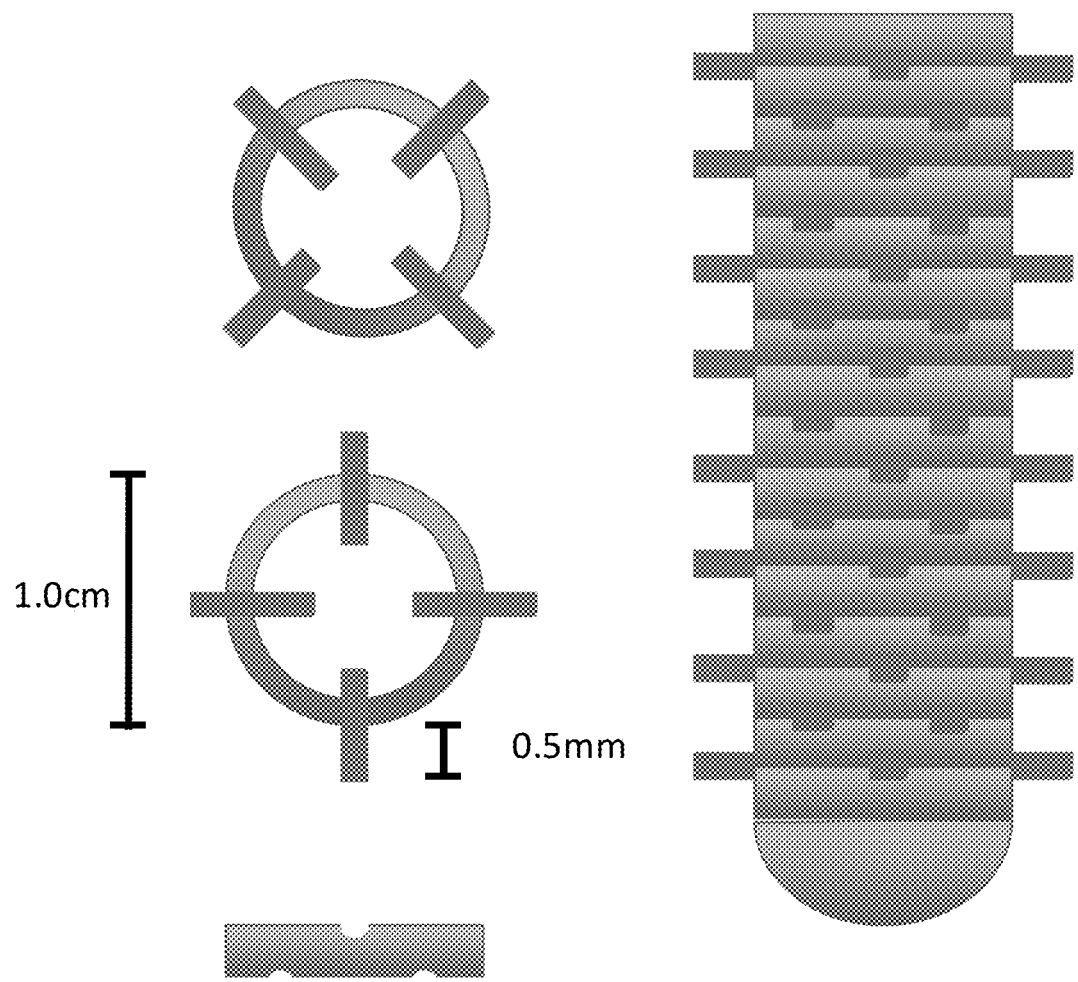
FIG. 4 depicts a schematic showing prototype 2.
Figure 5:
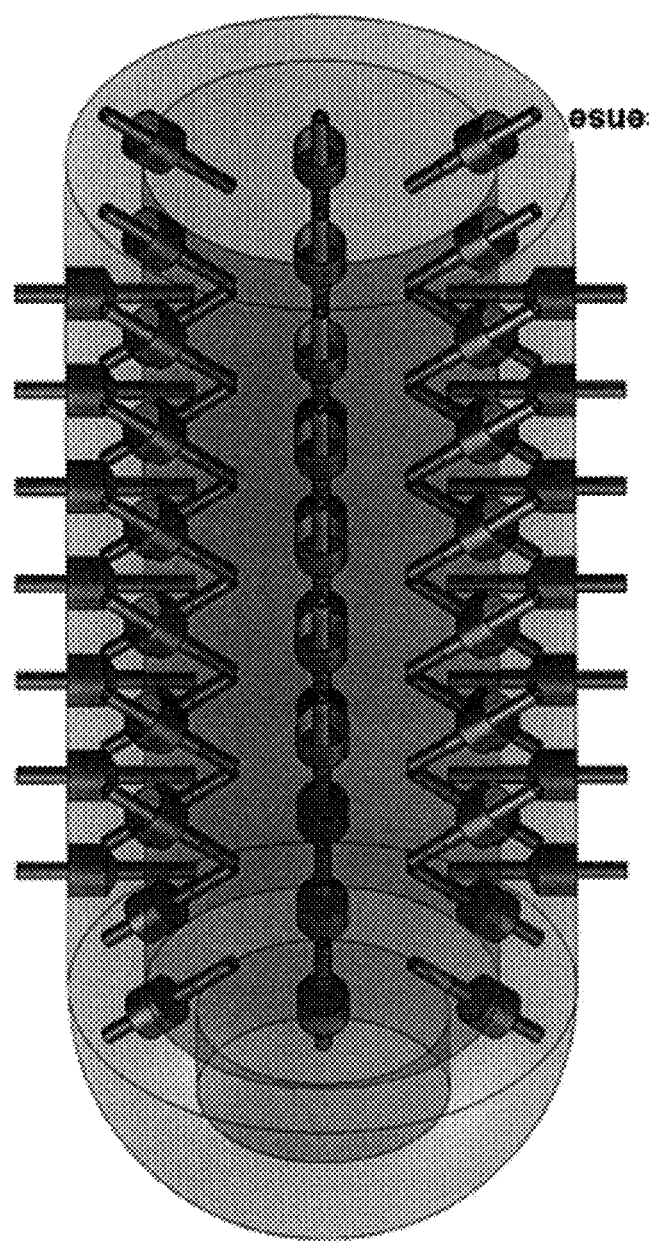
FIG. 5 illustrates a technical drawing of prototype 2.
Figure 6:
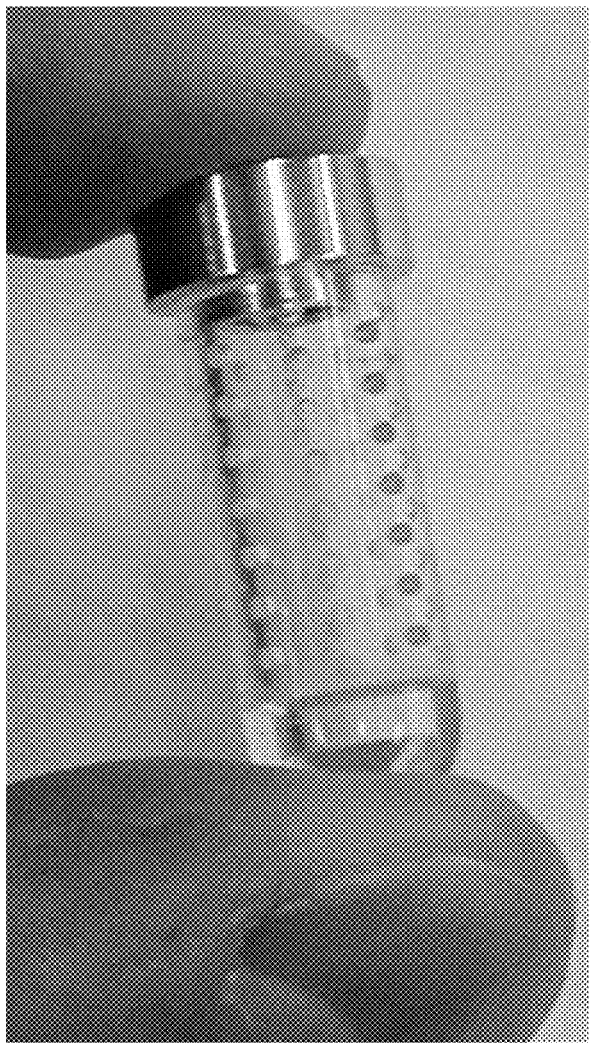
FIG. 6 shows a photograph of prototype 2, a 1× pill without needles.
Figure 7:
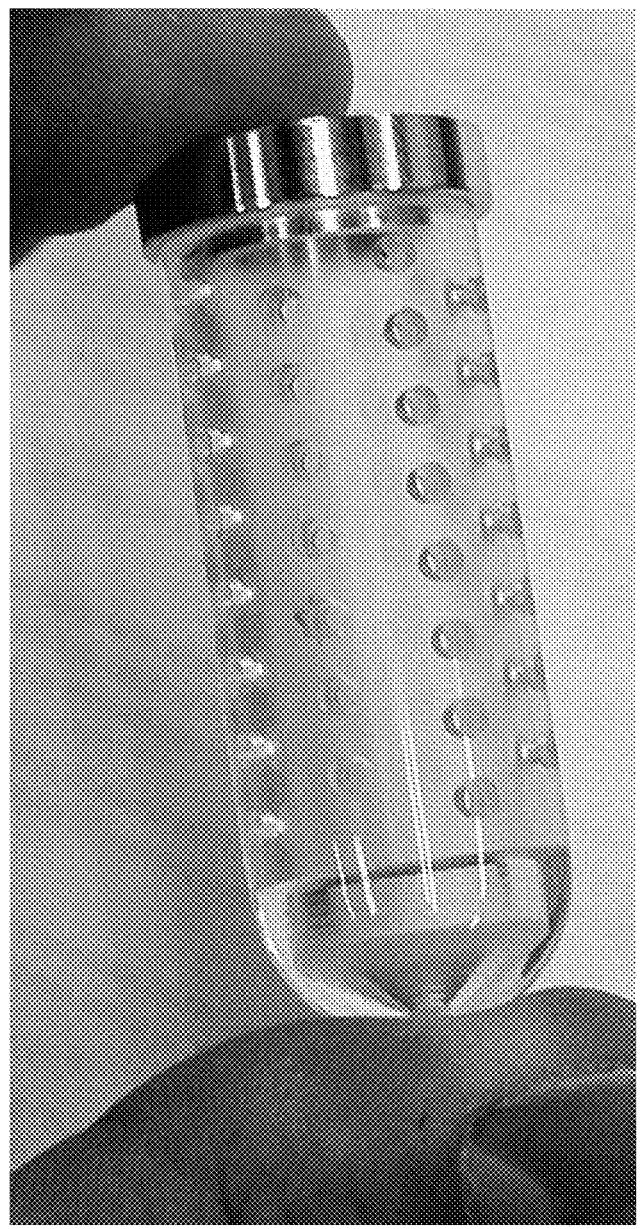
FIG. 7 shows a photograph of prototype 2, a 4× pill without needles.
Figure 8:
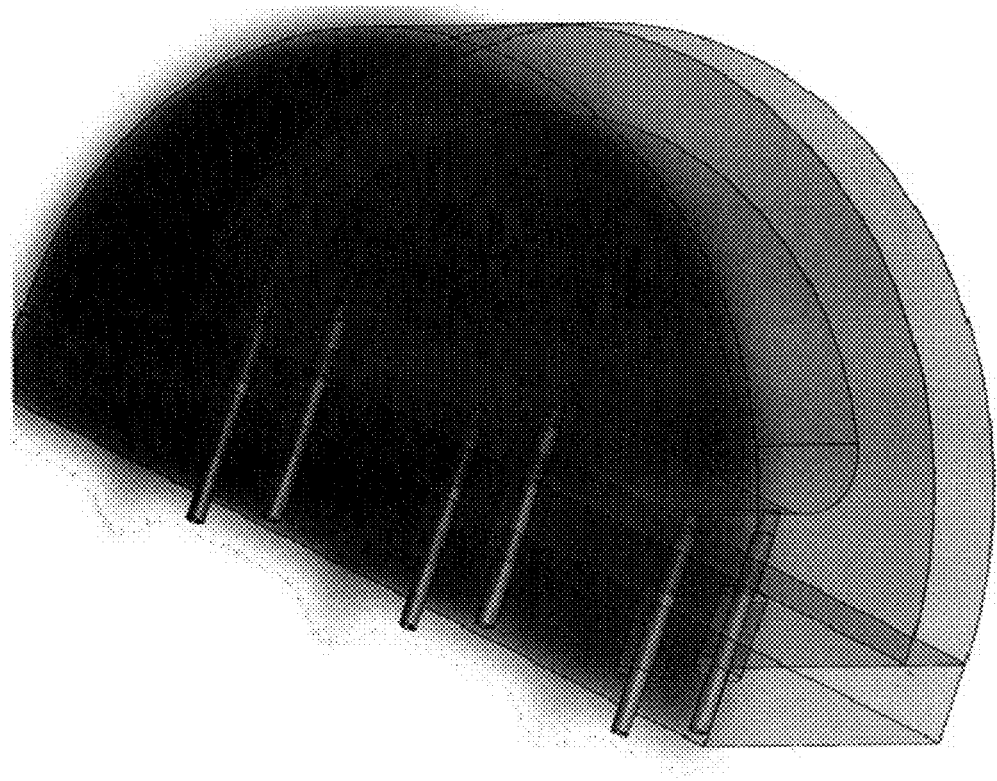
FIG. 8 illustrates a technical drawing of prototype 3.

In accordance with the present disclosure, a device can be arranged and constructed so that a plurality of microneedles protrude in different directions in three-dimensional space. In some embodiments, a device has a plurality of microneedles protruding radially. For example, as seen in FIGS. 3 and 4, microneedles can protrude radially from a device at an angle relative to the tangent to the device surface. Each microneedle of the plurality can independently have an angle of 90 degrees or any others less than about 90 degrees.

In some embodiments, a device can be arranged and constructed in a shape that comprises a plurality of faces defined with respect to one another by one or more edges so that a plurality of microneedles protrude from one or more faces. As illustrated in prototypes 1 and 3 (see, FIGS. 1-3 and 8), microneedles protrude from one face of the exemplary devices.

In some embodiments, the dimensions of a microneedle, or microneedles of a plurality thereof, are designed for the particular way in which it is to be used. Without wishing to be bound by any particular theory, parameters such as the length of an individual microneedle (i.e., the distance between the device surface where the microneedle protrudes from to the tip of the microneedle), and the shape/size of a microneedle (e.g., gauge size, tip shape, etc.) may influence the interaction of the microneedle, and thus the efficiency of delivery a payload or other functions of the device. In certain embodiments, part of a microneedle (e.g., a tip of a microneedle) can be or comprise a cube, a rectangle, a sphere, a cone, a pyramid, a cylinder, a tube, or any irregular shapes. In certain embodiments, a microneedle can be a barbed microneedle.

In some embodiments, the length of an individual microneedle may be about or less than about 10 cm, about 6 cm, about 5 cm, about 2 cm, about 1 cm, about 5 mm, about 2 mm, about 1 mm, about 500 µm, about 200 µm, about 100 µm, about 50 µm, about 20 µm, about 10 µm, about 5 µm, about 1 µm, about 500 nm, about 200 nm, about 100 nm, about 50 nm, about 20 nm, about 10 nm or even about 5 nm. In some embodiments, the length of an individual microneedle may be more than about 1 nm, about 5 nm, about 10 nm, about 20 nm, about 50 nm, about 100 nm, about 200 nm, about 500 nm, about 1 µm, about 5 µm, about 10 µm, about 20 µm, about 50 µm, about 100 µm, about 200 µm, about 500 µm, about 1 mm, about 2 mm, about 5 mm, about 1 cm, about 2 cm, about 5 cm, or about 6 cm. In some embodiments, the length of an individual microneedle may be within a range of about 2 cm and about 1 µm. In some embodiments, the length of an individual microneedle may be within a range of about 10 mm and about 50 µm. In some embodiments, the length of an individual microneedle may be within a range of about 5 mm and about 100 µm. In some embodiments, the length of an individual microneedle may be within a range of any two values above. It may be desirable, in certain embodiments, to adjust the length of a microneedle according to the application/use of the device and/or a payload delivered by the device. For example, to penetrate and/or abrade a mucus layer, in certain embodiments, the length of an individual microneedle may be within a range of about 2 mm and about 1 mm.

In some embodiments, a microneedle described herein includes a body. For example, a body can be tubular and it can be or comprise one or more nano/micro-tubes. Nano/micro-tubes can be fabricated using known techniques and materials in the art.

In some embodiments, the gauge (e.g., outer diameter) of an individual microneedle/tube may be about or less than about 2 cm, about 1 cm, about 5 mm, about 1 mm, about 500 µm, about 200 µm, about 100 µm, about 50 µm, about 20 µm, about 10 µm, about 5 µm, about 1 µm, about 500 nm, about 100 nm, about 10 nm or even about 5 nm. In some embodiments, the gauge of an individual microneedle/tube may be more than about 1 nm, about 5 nm, about 10 nm, about 100 nm, about 500 nm, about 1 µm, about 5 µm, about 10 µm, about 20 µm, about 50 µm, about 100 µm, about 200 µm, about 500 µm, about 1 mm, about 5 mm, or about 1 cm. In some embodiments, the gauge of an individual microneedle/tube may be within a range of about 1 cm and about 10 nm. In some embodiments, the gauge of an individual microneedle/tube may be within a range of about 1 mm and about 1 µm. In some embodiments, the gauge of an individual microneedle/tube may be within a range of about 1 µm and about 10 nm. In some embodiments, the gauge of an individual microneedle/tube may be within a range of about 5 nm to about 50 nm, about 50 nm to about 500 nm, about 500 nm to about 1 µm, about 1 µm to about 10 µm, about 1 µm to about 50 µm, about 50 µm to about 200 µm, about 200 µm to about 500 µm, about 500 µm to about 1 mm, or about 1 mm to about 5 mm. In some embodiments, the gauge of an individual microneedle/tube may be within a range of about 600 µm and about 10 µm. In some embodiments, the gauge of an individual microneedle/tube may be within a range of any two values above. In certain embodiments, nanotubes (e.g., carbon nanotubes) can be used as microneedles in accordance with the present disclosure.

In some embodiments, a microneedle described herein includes tip(s). In some embodiments, the dimension (e.g., a diameter) of a microneedle tip may be about or less than about 2 cm, about 1 cm, about 5 mm, about 1 mm, about 500 µm, about 200 µm, about 100 µm, about 50 µm, about 20 µm, about 10 µm, about 5 µm, about 1 µm, about 500 nm, about 100 nm, about 10 nm or even about 5 nm. In some embodiments, the dimension (e.g., a diameter) of a microneedle tip may be more than about 1 nm, about 5 nm, about 10 nm, about 100 nm, about 500 nm, about 1 about 5 about 10 about 20 about 50 µm, about 100 µm, about 200 about 500 about 1 mm, about 5 mm, or about 1 cm. In some embodiments, the dimension (e.g., a diameter) of a microneedle tip may be within a range of about 1 cm and about 10 nm. In some embodiments, the dimension (e.g., a diameter) of a microneedle tip may be within a range of about 1 mm and about 1 µm. In some embodiments, the dimension (e.g., a diameter) of a microneedle tip may be within a range of about 1 µm and about 10 nm. In some embodiments, the dimension (e.g., a diameter) of a microneedle tip may be within a range of any two values above.

Materials used for a microneedle or a portion of it may be selected and adapted for a particular use or design. A microneedle can be made of or comprises a payload (e.g., an therapeutic agent) ad discussed below in detail. For instance, a payload or an agent can be used in its crystallized or lyophilized state. Additionally or alternatively, a microneedle can comprise a degradable polymer. Without wishing to be bound by any particular theory, the degradable portion of a microneedle and the degradation rate may dictate the mechanism and efficiency of delivery a payload or other functions of the device.

Typically, a microneedle or a portion of it can comprise a degradable polymer. For instance, a microneedle can include or introduce a payload so that the payload is released after the degradation of the microneedle. In some embodiments, a microneedle described herein includes a base integrally connected to a device surface; the base comprising a degradable material. It is contemplated in the present application that the base of a microneedle degrades so that the microneedle is released from the device from which it protrudes and may remain lodged in the internal tissue after interaction and/or implantation. In certain embodiments, the microneedles lodged in the internal tissue may gradually degrade. In some embodiments, a microneedle includes a tip; the tip comprising a degradable material. It is also contemplated that the tip of a microneedle degrades so that only the tip of the microneedle breaks off.

Suitable degradable polymers, and derivatives or combinations thereof, as discussed above can be selected and adapted to have a desired degradation rate. Alternatively or additionally, a degradation rate may be fine-tuned by associating or mixing other materials as previously described (e.g., non-degradable materials) with one or more of degradable polymers.

In general, a degradation rate as used herein can be dictated by the time in which a material degrades a certain percentage (e.g., 50%) in a certain condition (e.g., in physiological conditions). In some embodiments, the degradation time of a device or at least one microneedle as described herein can have a wide range. In some embodiments, the degradation time may be greater than about 1 minute, about 5 minutes, about 30 minutes, about 1 hour, about 2 hours, about 5 hours, about 12 hours, about 24 hours, about 1.5 days, about 2 days, about 5 days, about 7 days, about 15 days, about 30 days, about 2 months, about 6 months, about 1 year, about 2 years, or even about 5 years. In embodiments, the degradation time may be about or less than about 10 years, about 5 years, about 2 years, about 1 year, about 6 months, about 2 months, about 30 days, about 15 days, about 7 days, about 5 days, about 2 days, about 1.5 days, about 24 hours, about 12 hours, about 5 hours, about 2 hours, about 1 hour, about 30 minutes or even about 5 minutes. The degradation time may be in a range of about 12-24 hours, about -6 months, or about 1-5 years. In some embodiments, the degradation time may be in a range of any two values above. Without wishing to be bound by any particular theory, controlled degradation can facilitate sustained release of payloads, in particular, over a prolonged period.

Payloads

Devices described herein can be dimensioned and constructed to comprise or carry one or more payloads. In some embodiments, a device can have a lumen bounded by a wall. Such a lumen can be used to carry a payload for delivery. In some embodiments, a portion of a device, for example, microneedles protruding from the device surface can be made of or comprise a payload as mentioned above. In some embodiments, all microneedles of the plurality or at least one microneedle may be hollow or porous constructed to carry or introduce a payload, which can be delivered to an internal tissue or through a vessel wall after interaction or even additional degradation of the microneedle. For example, a hollow microneedle or at least one of hollow microneedle of the plurality is cannulated, defining a channel that enables storage or introduction of a payload from the other parts of the device.

A payload can be in a gas form, a liquid form, a solid form or combinations thereof. In some embodiments, the volume of a payload may be about or less than about 50 mL, about 30 mL, about 20 mL, about 10 mL, about 8 mL, about 5 mL, about 4 mL, about 3 mL, about 2 mL, or about 1 mL. In some embodiments, the volume of a payload may be more than about 0.1 mL, about 0.5 mL, about 1 mL, about 2 mL, about 3 mL, about 4 mL, about 5 mL, about 8 mL, about 10 mL, about 20 mL or about 30 mL. In some embodiments, the volume of a payload may be in a range of about 0.1 mL to about 50 mL. In some embodiments, the volume of a payload may be in a range of about 1 mL to about 10 mL. In some embodiments, the volume of a payload may be in a range of about 2 mL to about 5 mL.

In certain embodiments, a payload of the disclosed device is carried in or transported through microneedles. An exemplary volume of a microneedle can be within a range of about 1 nL to about 1 µL.

In accordance with the present disclosure, a payload can include one or more agents for delivery after administration/implantation. A wide range of agents may be used. Agents may include, but are not limited to, therapeutic agents and/or an imaging agents. For example, agents may be or comprise any therapeutic agents (e.g. antibiotics, NSAIDs, angiogenesis inhibitors, neuroprotective agents, chemotherapeutic agents), cytotoxic agents, diagnostic agents (e.g. sensing agents, contrast agents; radionuclides; and fluorescent, luminescent, and magnetic moieties), prophylactic agents (e.g. vaccines), and/or nutraceutical agents (e.g. vitamins, minerals, etc.), or other substances that may be suitable for introduction to biological tissues, including pharmaceutical excipients and substances for cosmetics, and the like. In some embodiments, a payload include one or more bioactive agents.

An agent may be or comprise small molecules, large (i.e., macro-) molecules, any combinations thereof. Additionally or alternatively, an agent can be a formulation including various forms, such as liquids, liquid solutions, gels, hydrogels, solid particles (e.g., microparticles, nanoparticles), or combinations thereof.

In representative, non-limiting, embodiments, an agent can be selected from among amino acids, vaccines, antiviral agents, nucleic acids (e.g., siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, vitamins and/or any combination thereof. In some embodiments, an agent may be selected from suitable proteins, peptides and fragments thereof, which can be naturally occurring, synthesized or recombinantly produced.

In some embodiments, an agent is or comprises a cell. Such a device can be useful for the injection of whole cells (e.g., stem cells).

In some embodiments, an agent is or comprises a biologic. Examples of biologics including, but are not limited to, monoclonal antibodies, single chain antibodies, aptamers, enzymes, growth factors, hormones, fusion proteins, cytokines, therapeutic enzymes, recombinant vaccines, blood factors, and anticoagulants. Exemplary biologics suitable for use in accordance with the present disclosure are discussed in S. Aggarwal, *Nature Biotechnology*, 28:11, 2010, the contents of which are incorporated by reference herein.

In some embodiments, compositions and methods in accordance with the present application are particularly useful to deliver one or more therapeutic agents.

In some embodiments, a therapeutic agent is a small molecule and/or organic compound with pharmaceutical activity. In some embodiments, a therapeutic agent is a clinically-used drug. In some embodiments, a therapeutic agent is or comprises an anti-cancer agent, antibiotic, antiviral agent, anesthetic, anticoagulant, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

Exemplary anticancer agents included, but are not limited to, a cytokine, a chemokine, a growth factor, a photosensitizing agent, a toxin, an anti-cancer antibiotic, a chemotherapeutic compound, a radionuclide, an angiogenesis inhibitor, a signaling modulator, an anti-metabolite, an anti-cancer vaccine, an anti-cancer oligopeptide, a mitosis inhibitor protein, an antimitotic oligopeptide, an anti-cancer antibody, an anti-cancer agent, antibiotic, an immunotherapeutic agent, hyperthermia or hyperthermia therapy, a bacterium, radiation therapy and a combination of such agents. In some examples, an anticancer agent is cisplatin, carboplatin, gemcitabine, irinotecan, an anti-EGFR antibody, an anti-VEGF antibody and any combinations thereof.

A therapeutic agent used in accordance with the present application can be or comprise an agent useful in combating inflammation and/or infection. A therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof. Other anti-microbial agents such as copper may also be used in accordance with the present invention. For example, anti-viral agents, anti-protazoal agents, anti-parasitic agents, etc. may be of use. Additionally or alternatively, a therapeutic agent may be an anti-inflammatory agent.

A therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may a therapeutic gene as known in the art. In some embodiments, a therapeutic agent is a non-viral vector. Typical non-viral gene delivery vectors comprise DNA (e.g., plasmid DNA produced in bacteria) or RNA. In certain embodiments, a non-viral vectors is used in accordance with the present invention with the aid of a delivery vehicle. Delivery vehicles may be based around lipids (e.g., liposomes) which fuse with cell membranes releasing a nucleic acid into the cytoplasm of the cell. Alternatively or alternatively, peptides or polymers may be used to form complexes (e.g., in form of particles) with a nucleic acid which may condense as well as protect the therapeutic activity as it attempts to reach a target destination.

In addition or alternatively, a payload can include one or more surfactants. Various surfactants are known in the art and can be suitable for use as an enhancer to increase tissue permeability for delivery.

Coatings

In accordance with the present disclosure, devices described herein can comprise a coating. In some embodiments, the surface of a device is coated. In some embodiments, a portion of a device is coated, such as one or more microneedles. It will be appreciated that a coating may comprise one or more materials/units/layers.

In some embodiments, a coating is or comprise a payload, which may include one or more agents for delivery. A coating may be a medicated coating being made of or including an agent such as an anti-microbial agent. For example, an anti-microbial agent (e.g., gentamicin, clindamycin, copper, copper ions, silver) and/or a material with an ability to induce anti-microbial activity (e.g., gold that can be heated with an electromagnetic, magnetic, or electric signal) can be coated onto a device or a portion of a device. To give another example, a coating can be utilized to carry a payload/agent. In certain embodiments, an agent can be associated with individual layers of a multilayer coating for incorporation, affording an opportunity for exquisite control of loading and release from the coating. For instance, an agent can be incorporated into a multilayer coating by serving as a layer. Exemplary coatings suitable for use are discussed in US 20080311177, the contents of which is incorporated by reference herein.

In some embodiments, a coating is or comprise a material for the purpose other than medication. For example, an inert coating, optionally with a good taste, can be used to assist swallowing. Such coatings or materials can be used in combination with any other coating disclosed therein.

In some embodiments, a coating is or comprise a targeting material such as antibodies, aptamers). Such coatings or materials can be used in combination with any other coating disclosed therein.

In some embodiments, a coating is or comprise an adhesive material as discussed above. For example, a coating can be or comprise a bioadhesive such as chitosan and carbopol. Such coatings or materials can be used in combination with any other coating disclosed therein.

Additionally or alternatively, a device with a coating can be arranged and constructed so that the device transitions from an initial state to an exposed state. For example, a coating may be degradable so that when it is removed microneedles protruding from the device surface are exposed. To give but another example, a coating may maintain but microneedles protruding from the device surface become exposed upon triggering. For instance, a coating can be a pH-sensitive coating, an inflammatory-sensitive coating, a virus/bacteria-sensitive coating, a hydrolytically degradable coating, a cancer specific coating (e.g., coatings in response to cancer specific proteases allowing for targeted delivery) or any combinations thereof. In certain embodiments, a device described herein without a coating can also be arranged and constructed so that the device transitions from an initial state to an exposed state upon triggering. Typical triggering mechanisms and suitable materials to use are discussed in detail in the section below.

In an initial state, the length of an individual microneedle may be about or greater then zero. In an exposed state, the length of an individual microneedle may be longer than the one in the initial state. Similar to the discussion above, the length of an individual microneedle in an exposed state may be about or less than about 10 cm, about 6 cm, about 5 cm, about 2 cm, about 1 cm, about 5 mm, about 2 mm, about 1 mm, about 500 μm, about 200 μm, about 100 μm, about 50 μm, about 20 μm, about 10 μm, about 5 μm, about 1 μm, about 500 nm, about 200 nm, about 100 nm, about 50 nm, about 20 nm, about 10 nm or even about 5 nm. In some embodiments, the length of an individual microneedle in an exposed state may be more than about 1 nm, about 5 nm, about 10 nm, about 20 nm, about 50 nm, about 100 nm, about 200 nm, about 500 nm, about 1 μm, about 5 μm, about 10 μm, about 20 μm, about 50 μm, about 100 μm, about 200 μm, about 500 μm, about 1 mm, about 2 mm, about 5 mm, about 1 cm, about 2 cm, about 5 cm, or about 6 cm. In some embodiments, the length of an individual microneedle in an exposed state may be within a range of about 6 cm and about 1 µm. In some embodiments, the length of an individual microneedle in an exposed state may be within a range of about 10 mm and about 50 µm. In some embodiments, the length of an individual microneedle in an exposed state may be within a range of about 5 mm and about 100 µm. In some embodiments, the length of an individual microneedle in an exposed state may be in a range of any two values above.

Activation

A device described herein, in noted previously, can be activated to expose or extend microneedles upon triggering, so that the exposed/extended microneedle can penetrate and/or abrade an internal tissue of a subject or a wall of a vessel. Additionally or alternatively, a device described herein can be activated to penetrate and/or abrade an internal tissue of a subject or a wall of a vessel by microneedles protruding from the device surface and/or deliver a payload after the interaction. Typically, such a device transitions from an inactivated phase to an activated phase. In certain embodiments, an activation is reversible. For example, devices can be activated to expose one or more microneedles in an activated phase and the microneedle can retracted to an inactivated phase.

Activation can be achieved by utilizing suitable device materials and payloads with controllable swelling, diffusion, erosion rate, loading profiles or other properties. In some embodiments, a device can simply be activated and start to function within a certain time period or at a certain rate once administrated/implanted. For example, swellable hydrogels and/or degradable polymers can be used. Typically, the swelling/degradation of materials can be tuned by materials and design.

In some embodiments, a device can comprise a regulated pump, which may be controlled by an internal or external force. To give an example, osmotically driven pumps, which is typically operated in the presence of water and independent of gastric pH and hydrodynamic conditions, can be used.

In addition or alternatively, a device can be activated by a trigger (e.g., internally and/or externally) using a wide range of techniques known in the art (see, A. *Anal, Recent Patents on Endocrine, Metabolic & Immune Drug Discovery,* 2007, 1, 83-90, the contents of which is incorporated by reference herein). In some embodiments, devices can be activated in response to stimuli including the presence of absence of blood, specific molecules/entities (e.g., cancer proteases, virus, bacteria, inflammatory cytokines and cells), magnetic fields, ultrasound, electric fields, pH, temperature, light, mechanical forces, or any combination thereof. Treatment of diabetes with insulin can be an example, where such devices are expected to be beneficial. In certain embodiments, payloads can be delivered in a pulsatile fashion.

In some embodiments, activation of a device can be induced by a stimulus. For example, suitable polymers can be used in a device that can undergo phase transitions and demonstrate swelling-deswelling changes in response to environmental changes including, but not limited to, pH, ionic strength, temperature, electric fields, magnetic fields, light, ultrasound, and audible sound (e.g., a ring tone). In certain embodiments, a device can be activated (e.g., triggered) by a signal from a wireless device (e.g., a phone or other electronic devices). In certain embodiments, a device can be responsive to pH. A pH-responsive device may arrive in a small bowel after approximately two hours of transit time and be activated by a pH change.

Responsive payload release from devices as described herein may result from the stimuli-induced changes in gels or in micelles, which may deswell, swell, or erode in response to respective stimuli. The mechanisms of the release may include ejection of agents from the gel, agent diffusion along a concentration gradient, electrophoresis of charged agents towards an oppositely charged electrode and/or liberation of an entrapped agent as the gel or micelle complex erode.

Thermo-responsive devices can be used when temperature is a trigger. For instance, a thermo-responsive device may be activated once lodged at a target site (e.g., a site of disease with an elevated temperature). Thermo-sensitive polymers and corresponding hydrogels that undergo reversible volume changes in response to change in temperature can be suitable for use in accordance with the present application. Typical thermo-sensitive polymers include poly (N-isopropylacrylamide) (PNIPPAm) and its copolymers with others (e.g., PEG).

Electro-responsive devices can be used when an electric field is an external stimulus. In general, electrically responsive materials are polyelectrolytes and may thus be pH-responsive as well as electro-responsive. Synthetic as well as naturally occurring polymers, separately or in combination, can be used in accordance with the present application. Examples of naturally occurring polymers include, but are not limited to, hyaluronic acid, heparin sulfate, chondroitin sulfate, agarose, carbomer, xanthan gum and calcium alginate. Synthetic polymers can be acrylate and methacrylate derivatives such as polydimethylaminopropyl acrylamide.

Magnetically responsive devices can be used when a magnetic field is a trigger. Devices provided herein may comprise one or more ferrimagnetic, ferromagnetic, paramagnetic, and/or superparamagnetic materials, which are magnetically responsive. Examples include, but are not limited to, iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. In certain embodiments, an external magnet may be used to facilitate the interaction of at least one microneedle of the device. As an example, a magnetically responsive device is illustrated in Example 1.

Uses and Applications

Provided are devices and methods that can be used in various applications. Provided devices and methods, in general, may be used as or in a delivery system (e.g., a pill, an implant, etc.) and can release payloads during/after administration/implantation. Exemplary administrations include but are not limited to oral, intravenous, sublingual (i.e., under a tongue), respiratory, or intraoperative administrations. It is recognized in the present application that provided devices and methods can be of particular interest in and surprisingly useful for oral or intravenous administration.

In certain embodiments, provided devices and methods can be used in treating respiratory conditions. For example, devices can be adapted and dimensioned to be inhaled and the route of administration would be via an inhaler or nebulizer. Such devices can access a tissue in respiratory systems such as tissues in larynx, bronchial tree, lungs, alveoli, etc. The dimensions of such devices can be within a range of about 100 nm to about 100 µm, about 500 nm to about 10 µm, or about 1 µm to about 5 µm.

In certain embodiments, provided devices and methods can be used in intraoperative administration. Any area of a subject may be accessible, such as, an intraperitoneal, space, joint space, brain, etc.

In other embodiments, provided devices and methods can be used as or in implants. For example, provided devices and methods can be useful for a suppository or pessary such as a rectal, vaginal, urethral and bladder suppository or pessary. To give another example, a device can be implanted on the exterior and/or interior side of a stomach, heart, pancreas, liver or other organs.

As noted previously, a device can be dimensioned and constructed to carry a payload as described previously, which payload is delivered to an internal tissue of a subject or a wall of a vessel after interaction with microneedles protruding from the device surface. In will be appreciated that devices and methods provided herein can be useful, in particular, in delivery of a variety of macromolecular, potent therapeutic agents, which may suffer from poor permeability across biological membranes/tissues. As note above, exemplary biologics suitable for use in accordance with the present disclosure include, but not limited to monoclonal antibodies, single chain antibodies, aptamer, enzymes, growth factors, hormones, fusion proteins, cytokines, therapeutic enzymes, recombinant vaccines, blood factors, and anticoagulants.

A target subject or site in accordance with the present disclosure can be a viscus. In some embodiments, a viscus is an abdomen selected from the group consisting of peritoneum, stomach, duodenum, intestine, colon, liver, spleen, pancreas, kidney, adrenal gland, appendix and gall bladder. In some embodiments, a viscus is selected from pelvis, coccyx, ovaries, fallopian tube, uterus, clitoris, perineum, urinary bladder, testicle, rectum, and vagina.

In certain embodiments, a subject can be a part of a nervous system. For example, a spinal cord, nerve, or brain can be a subject. It is contemplated that a device disclosed herein can circulate in the cerebrospinal fluid and optionally can deliver a payload to a targeted area.

In certain embodiments, a subject can be a joint, spine or disk.

Exemplary internal tissues of a subject, such as a mammal (e.g., human), includes any internal tissues in gastrointestinal (GI) tract, large or small intestine (jejunum, duodenum), stomach, esophagus, buccal or mouth tissue. As an example, a mucous membrane, including buccal mucosa, esophageal mucosa, gastric mucosa, intestinal mucosa, nasal mucosa, olfactory mucosa, oral mucosa, bronchial mucosa, uterine mucosa, etc., can be an internal tissue. In some embodiments, internal tissues can be various types of carcinoma, metastases, tissues undergoing restenosis, inflamed tissue, and the like tissues.

In addition to delivering a payload or as an alternative, devices and methods disclosed herein can be used for sampling. In some embodiments, a device can be used to aspirate a material (e.g., bodily fluids and/or cells) as it travels or remains lodged internally in a subject (e.g., human) for diagnostic purposes. A device can be used for monitoring of chronic diseases. For example, the identification of inflammatory cells, and/or the diagnosis of cancer can be performed utilizing the devices/methods provided herein by sampling the environment (e.g., blood, tissue, etc.) for cancer cells, DNA, RNA or any analytes.

EXEMPLIFICATION

Example 1: Magnetically Responsive Device

Figure 9:
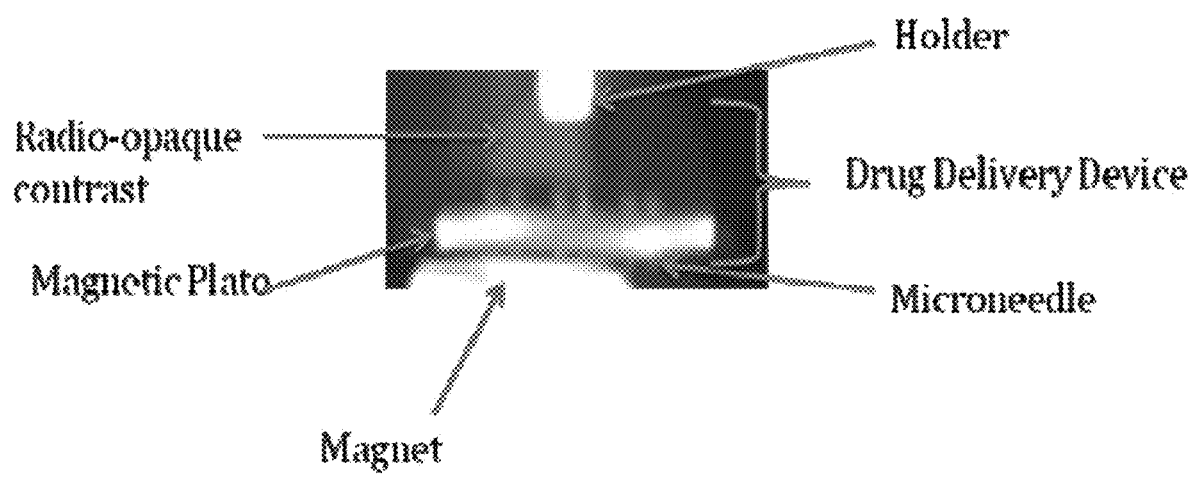
FIG. 9 shows an image of a magnetically responsive device used in a magnetic field, obtained using computer tomography (CT imaging).

FIG. 9 shows an exemplary magnetically responsive device and the evaluation of the effect of a magnetic field. In order to evaluate the juxtaposition of microneedles to soft tissue (porcine small intestine), a magnetically responsive device fitted with a magnetic plate was placed overlying the luminal side of the porcine small intestine. A magnet was placed on the outer surface of the intestine and images obtained using computer tomography (CT imaging). Close juxtaposition of the magnet to the microneedles was observed ensuring close approximation to the intervening tissue.

Example 2: Visualization Studies

Using porcine gelatin, the effects of a microneedle prototype device was evaluated. Specifically, porcine gelatin was prepared at a concentration of 1.5% to mimic the density of gastrointestinal tissue. The gelatin provided the added benefit of allowing the application site to be visualized. A prototype device filled with a solution of 0.025% allura red dye was applied to the gel and a volume of 100-300 microliters of dye was injected. A second device lacking the needles was also used as a control.

Figure 10:
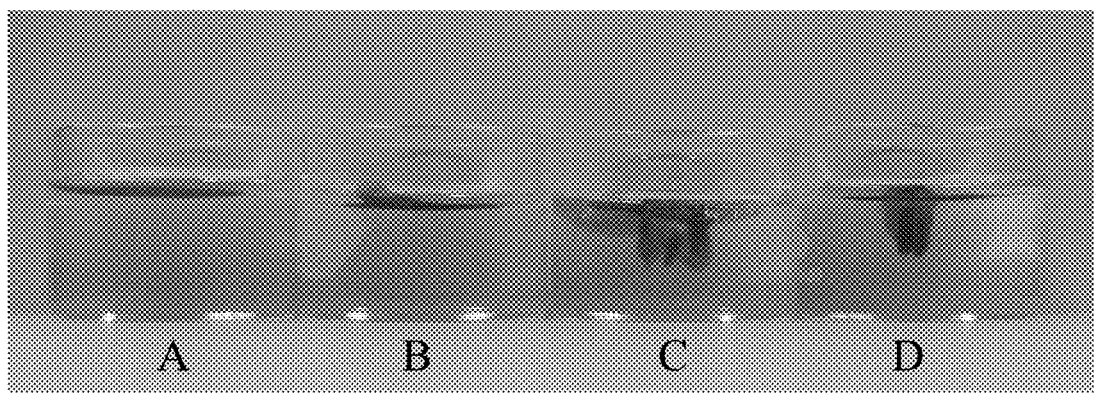
FIG. 10 shows a photograph of porcine gelatin cups that have been treated with the needleless control device (A and B) and with the microneedle-containing device (C and D) visualized from the side. The red dye seen in A and B is on top of the gel and did not make it into the gel-matrix. In C and D this same pool is seen on the top but there are also clear sites of dye penetration into the gel corresponding to the site of needle penetration.
Figure 11:
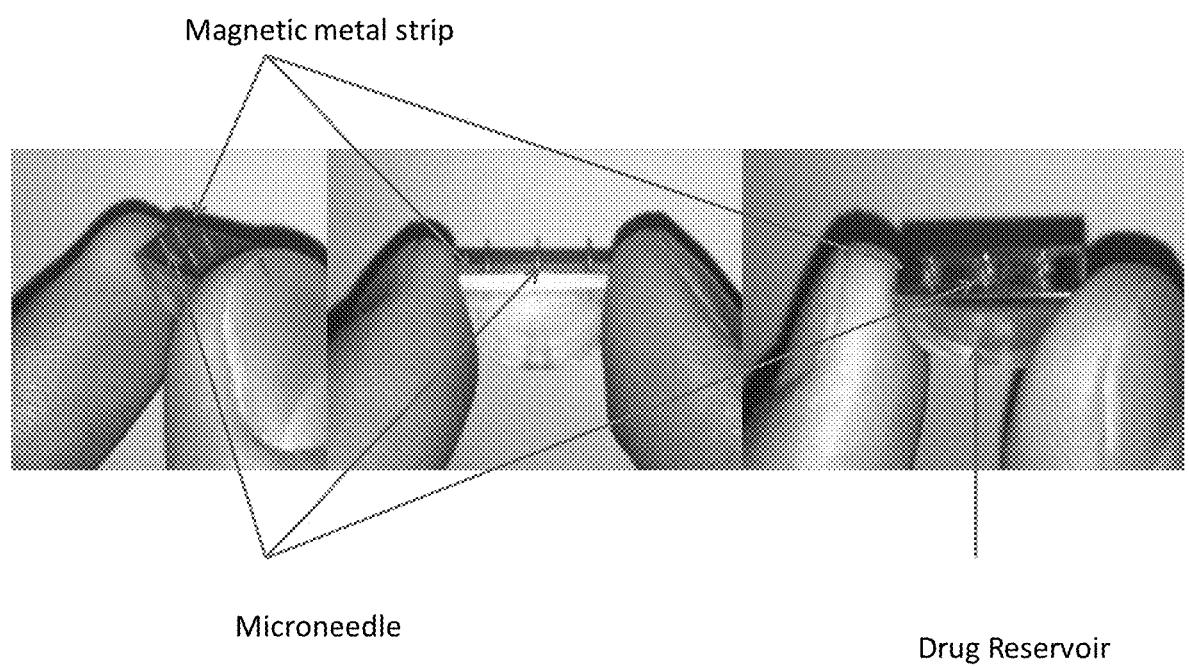
FIG. 11 shows photographs of prototype 3 with a magnetic strip.
Figure 12:
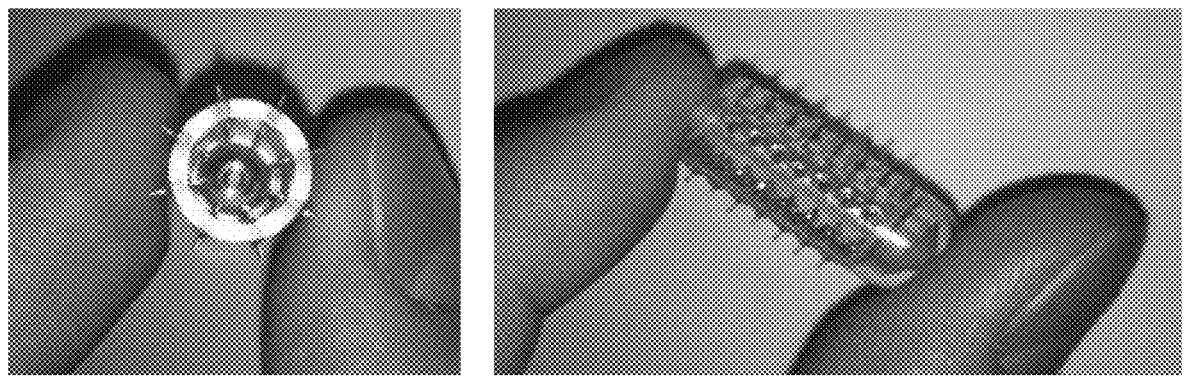
FIG. 12 shows photographs of prototype 2 having a radial distribution of microneedles on the device surface with the reservoir visible and in direct continuity with the outside of the pill via the microneedles (see left panel for cross sectional view).

As shown in FIG. 10, the device with microneedles (C and D) enabled permeation of the dye into the gel matrix whereas absence of the needles (A and B) simply resulted in expulsion of the dye over the gel surface. This highlights the efficacy of the microneedle device in deeper tissue penetration of the model drug compared to simple diffusion (simulated by the control device shown in FIGS. 10 A and B).

Example 3: Animal Tests

Experiments for drug uptake by a local injection into the GI tract of animals were conducted using devices that comprise microneedles in a plastic holder exposing the tips 600 µm out.

Our device is capable of enhancing the uptake of molecules through the gastrointestinal (GI) tract as well as image the GI tract. Therefore our aims for the in vivo testing include: 1) Evaluate the safety of the device in vivo; and 2) Evaluate the efficacy of the device in vivo through the administration of drugs with the aid of the device.

Scientific Merit

The goal of our research lies in enabling the oral administration of drugs that currently are administered via the intravenous/subcutaneous/intramuscular routes. Utilizing the provided device to enhance the uptake of drugs through the GI mucosa would represent a significant contribution in the field of medicine.

Animal Model

We have chosen the porcine model due to its close anatomical similarity to the human gastrointestinal tract. Through our experiments with pig tissue, we test the feasibility of delivering drugs to the GI tract using microneedles.

Implantation Study

1) Safety evaluation: a total of 10 animals will be required to establish initial proof of safety of the device in a large mammal. These studies will be focused on evaluation of obstruction from our device. Two of the 10 animals will be euthanized following passage of the device for histological evaluation of the tissue. The remaining 8 will be evaluated closely for signs of infections.

2) Efficacy evaluation: we have carried out extensive ex vivo/in vitro experiments on the GI tracts of pigs and have observed a significant level of variability between the intestines of pigs which has helped inform our in in vivo experimentation. This has translated on requiring an extensive number of experimental repeat with a total of 18 animals required. Fortunately we are able to use the remaining 8 animals from the safety studies in subsequent efficacy studies therefore requiring an additional 10 animals.

We are planning the evaluation of multiple different drugs with our delivery device (note: glucose is used to counteract hypoglycemia induced via insulin administration). These drugs will encompass 3 major drug classes including biologics (with varying in molecular weight from insulin to infliximab), steroids and small molecule anti-inflammatory (i.e. mesalamine). The delivery of each drug will be carried out in 6 separate animals which will be treated and evaluated with the same drug and the same device. For example 6 pigs will be treated with device-based delivery of insulin in week 1 and with injection-based delivery of insulin in week 2. We are planning on starting our experiments with the drugs with the lowest molecular weight (i.e. octreotide, oxytoxin, hydrocortisone and mesalamine) to establish proof of concept. Depending on the success with these we plan to proceed to further testing with the larger drugs (i.e. rituximab, infliximab).

For all procedures the animals (pigs) will be anesthetized by DCM personnel. Procedures requiring anesthesia include: blood draws, endoscopy, device placement, radiography (x-ray evaluation) and diagnostic ultrasound. This will include anesthesia with telazol 4-6 mg/kg and xylazine 2 mg/kg. Frequency of dosing will be per DCM personnel.

1) Safety evaluation:

a. Pigs will be allowed 72 hours to acclimate to their new surroundings.

b. On arrival from Parson's Farm all animals will be evaluated with fecal ova and parasite analysis and will be treated under DCM guidelines. Additionally all animals will be evaluated with a complete blood count and chemistry panel as well as initial abdominal and chest x-ray. Blood draws will be performed via venous sampling from the ear. This will allow us to ensure healthy animals prior to the initiation of any intervention. Blood collection will be performed with the use intramuscularly administered mild sedatives, i.e. telazol 4-6 mg/kg and xylazine 2 mg/kg. The total amount of blood drawn will not exceed 5 ml which is sufficient for basic complete blood count analysis and chemistry panel evaluations.

c. Animals will be kept free from any solid food ingestion for 8 hrs prior to endoscopy to minimize aspiration risks during general anesthesia and endoscopy.

d. The device will be introduced endoscopically and guided/placed in the pig's stomach. There it will be released to travel down the porcine GI tract.

e. The pig will be imaged serially with either x-rays, ultrasound or floruoscopy (CT if available) every hour to document transit of the capsule through the GI tract. Animals will be imaged for a maximum of 8 hours in one 24 hour period. Given the need for repeated imaging the animals will be kept anesthetized by DCM personnel for a maximum of 8 hours. Irrespective of whether the device (pill) has passed the animal will be awakened after a maximum of 8 hours. During general anesthesia animals will be kept warm and hydrated intravenously through the administration of either lactated Ringer's solution or normal saline per DCM personnel. General anesthesia will be limited to twice a week with a minimum interval of 72 hours between procedure to ensure adequate recovery from anesthetics. If the drug-delivery device has not passed at the end of the procedure animals will be re-evaluated with imaging (either diagnostic ultrasound or radiography) 12-24 hours after placement of the drug delivery device. Every effort will be made to use acclimating techniques such as back rubbing or abdominal rubs that are reported to make animals more docile and cooperative while performing diagnostic ultrasonography. Should the device not be passed within 24 hours light sedation will be instituted 24 hours later for repeat imaging. Imaging will be coordinated with DCM veterinary staff. The animals will be monitored every 12 hours until the device is passed for any clinical signs of intestinal obstruction (e.g. loss of appetite, grunting, vomiting, abdominal distension) and should these be noted they will be euthanized by DCM staff.

f. Following passage of the device the pig will be euthanized by DCM staff and the GI tract isolated for complete histological evaluation. The device will be isolated from the feces. Two animals will be euthanized following the passage of the capsule for histological evaluation of their tissues.

g. A separate cohort of pigs may be evaluated with blood cultures for monitoring of possible bacteremia. Blood cultures will be performed daily for 72 hours following device exposure. Blood (5 ml) will be collected via venopuncture of the ear using at 21-23 gauge needle. Following device exposure animals will be monitored daily for any temperature changes suggestive of fever. Blood collection will be performed with the use intramuscularly administered mild sedatives, i.e. telazol 4-6 mg/kg and xylazine 2 mg/kg.

2) Efficacy evaluation:

a. Pigs will be restricted from oral solid food for the preceding 8 hours prior to any endoscopic procedure and/or general anesthesia to minimize aspiration risks.

b. The device will be introduced endoscopically and placed against the esophagus/stomach/duodenum/colon/sublingual (under the tonge)/vaginally. At these sites a volume of 50 ml of test drug will be used to bathe the area and the pill activated to allow for delivery of the drug. All endoscopic procedures will be performed with general anesthesia which is to be administered by DCM personnel. Anesthetics planned for this include telazol 4-6 mg/kg and xylazine 2 mg/kg.

c. Prior to the delivery of drug from the device a catheter will be placed in the femoral/internal jugular vein of the pig by DCM staff using the Seldinger technique to allow for frequent blood sampling. A 9 gauge catheter will be used. The placement and type of catheter is similar to that used in humans for central access. During the administration of the drug as well as following drug administration 2 ml of blood will be sampled every 5 minutes through the catheter for a total of 2 hours (total of 48 ml). This volume is well within the limits of 15% of total blood volume. For a 50 kg pig we estimate a total blood volume of 50 kgx7%=3.5 L of which 15% represents approximately 520 ml of blood which could be sampled every 2 weeks.

d. As a control the drug being evaluated will be injected in the adjacent area on a separate experimental day. Please note that injections in the GI tract are commonly used in humans. Blood collection will be performed as delineated in the section, i.e. section 4/2c.

Endoscopy carries inherent risks with its performance including perforation, bleeding, and infection. In order to minimize the risks of endoscopy a gastroenterology fellow from the Massachussetts General Hosptal (Dr. Traverso) will perform all endoscopy techniques. Pigs will be monitored by Drs. Schroeder and Traverso as well as DCM staff during the procedure. Furthermore they will be evaluated twice a day following endoscopic interventions.

Animals will be monitored for appetite, vomiting, diarrhea, melena, hematochezia and general activity level.

Implantation Procedures

The device will be sterilized in bleach, then ethanol, then water for injection (for wash). The device cannot be heated to high temperatures.

The implant will be placed for 1 hr and then removed. Aseptic technique will be used to prevent any infection or inflammation.

As noted above for the safety evaluation of the device the device will be allowed to freely pass through the entire gastrointestinal tract of the pig. Passage of the pill is

| Compound | Dose (per animal or per kilogram) | Dose Volume (US/Injectable) | Frequency and Duration of Dosing | Known Toxic Levels |
|---|---|---|---|---|
| Insulin | 0.2-0.5 units/kg | 10 mL/0.5 mL | Up to three times/eight hours | Onset of hypoglycemia, can treat with glucose |
| Glucose | 5-50% Solution | N/A/1 L | As needed for treatment of hypoglycemia | >5000 mg/kg |
| Oxytocin | 10 units/animal | 50 mL/1 mL | 0.5 mU/min | >10,000 units/kg |
| Vasopressin | 40 units/animal | 10 mL/1 mL | 6 Doses/day | >2 mg/kg (>1200 units) |
| Hydrocortisone | 200 mg/animal | 50 mL/1 mL | 3 Dose/day | 5000 g/kg |
| Budesonide | 3-50 mg/animal | 50 mL/1 mL | 1 Dose/day | 3200 mg/kg |
| Mesalamine | 4 g/animal | 50 mL/1 mL | 1 Dose/day | 2800 mg/kg |
| Erythropoietin | 60,000 units/week | 50 mL/1 mL | 1 Dose/week | >100,000 units |
| Octreotide | 250 mcg/animal | 2.5 mL/1 mL | 3 Doses/day | >20 mg/kg Fatal |
| Pramlintide | 60 mcg/animal | 50 mL/0.1 mL | Up to 3 Doses/day | >600 mcg/kg/day |
| Interferon | 180 mcg/animal | 50 mL/1 mL | 1 Dose/week | >6750 mcg/kg |
| Infliximab | 10 mg/kg | 50 mL/0.5 mL/kg | Once | >20 mg/kg no direct toxic effect observed |
| Rituximab | 1 g/animal | 100 mL/10 mL | Infusion, 50 mg/hour | >5 g/animal |
| Etanercept | 50 mg/animal | 50 mL/1 mL | Weekly | >1000 mg/animal |

The device will be administered to Yorkshire pigs.

Site(s) of implantation:

The device will transiently pass through the animals gastrointestinal (GI) tract (from the mouth to the anus). It may become positioned in juxtaposition against the following tissues along the GI tract. These include: sublingually (under the tongue), in the esophagus, in the stomach, in the duodenum and in the colon and rectum. Aside from the GI tract the device may also be used in the vagina of female animals.

Please note that the device may be held against the anatomical structures named above for the evaluation of drug delivery as part of the efficacy studies of this device. The device will be removed at the end of each drug delivery experiment, optionally with the aid of the endoscope. As part of the safety studies, the device will be allowed to pass through the entire gastrointestinal tract and collected subsequently from the animals excrement. Size and weight of device:

Size: 3 cm long, 1.5 cm in diam.

Weight: below 10 grams.

Composition and biocompatibility of device:

The device is intended to be swallowed and excreted with the feces.

The device is coated with a plastic coating and is made of biocompatible materials.

The device is made with dimensions and composition similar to those of the Given Imaging Capsule which is FDA approved and currently widely used in humans for imaging of the GI tract.

expected after 6-8 hours of placement (this is based on human passage of similarly designed pills).

The animals will be monitored throughout the experiment by a DCM vet.

The animals will be anesthetized during endoscopy by DCM staff. No pain is expected due to the implantation due to the fact that no sensation exists in this location.

Exemplary compounds listed in table below will be used in administration.

No toxicity is expected at the indicated doses of the compounds. Persistent dosing with these agents maybe associated with clinical signs which are as follows:

Insulin: Reduces glucose levels in the blood.

Oxytocin: Initiates and strengthens uterine contractions.

Vasopressin: Reduces postoperative abdominal distention.

Hydrocortisone: No effect, steroids generally require long-term use for signs to develop. Steroids at higher doses may induce sleep and or mood disturbances but these effects are not anticipated that the administration levels proposed above.

Budesonide: Steroid, no effect.

Mesalamine: Anti-inflammatory.

Vancomycin: Anti-bacterial agent.

Octreotide: Reduces blood levels of growth hormone and IGF-I.

Pramlintide: Administered with insulin for better glucose control.

Interferon: no overt clinical sign. Used to augment immune response in hepatitis and cancer.

Infliximab: anti-inflammatory agent used in inflammatory bowel disease, psoriasis.

Rituximab: Reduces symptoms of rheumatoid arthritis.

Etanercept: Reduces symptoms of rheumatoid arthritis.

Close monitoring (twice a day) will be instituted following administration of these agents. Specifically, signs that will be monitored include nausea, vomiting, infection, fever, and lethargy. The one agent which we expect to have an effect is insulin. Therefore, glucose will be closely monitored from the blood draws. If a significant drop in glucose is observed, a bolus of glucose will be administered per DCM guidelines.

Compounds are pharmaceutical-grade, or provide justification for using non-pharmaceutical grade compounds in animals. Justification should include scientific necessity and non-availability of pharmaceutical-grade equivalent. Investigator must provide assurance that non-pharmaceutical compounds will be prepared sterile if delivered by injection (describe sterility methods; e.g., 0.22 micron filtration) and be labeled with a reasonable expiration date.

All administered drugs will be pharmaceutical-grade and all injections will be sterile.

Example 4: Swine Animal Model

The swine animal model has been identified as the optimal model for the evaluation of micronoeedle-based technologies and thus has been used in this Example. This is largely in part for the similarities in the anatomy and dimensions of the swine gastrointestinal tract (GIT) to that of humans.

Yorkshire swine approximately 70 kg in weight were fasted overnight. The animal was sedated and a femoral venous catheter placed to enable frequent blood sampling for glucose monitoring. An endoscope was introduced orally or rectally depending on the tissue being accessed. Oral access for the stomach and small intestine and rectal access for the colon.

Utilizing a Carr-Locke needle, 10 units of insulin aspart (Novolog®) were injected at different sites within the gastrointestinal tract including the stomach and duodenum. Glucose levels were monitored by frequent blood sampling via the femoral venous catheter with the aid of a glucometer.

Control experiments were carried out by delivery of 10 units of insulin aspart (Novolog®) without the use of the needle.

Figure 13:
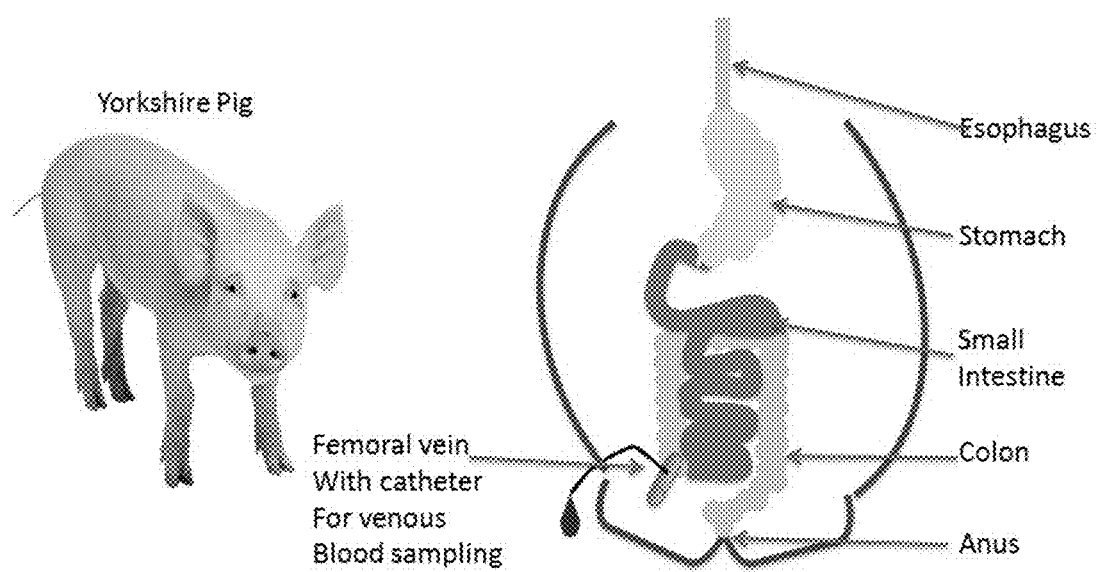
FIG. 13 illustrates a schematic of the experimental set-up for the swine animal model used in Example 4.

Referring to FIG. 13, the right panel depicts the basic experimental setup which includes having the animal in the supine position with a central venous catheter placed in the femoral vein to enable rapid and frequent blood monitoring. Access to the GIT is either through the mouth which renders the esophagus, stomach and small intestine accessible to microinjection or via the anus which gives access to the colon.

Figure 14:
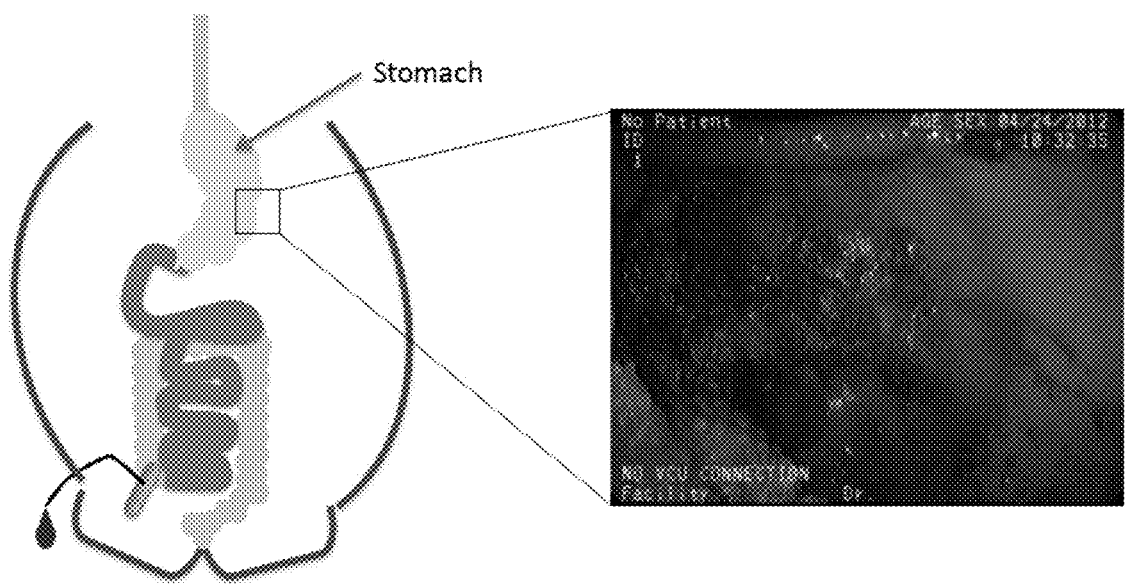
FIG. 14 shows a schematic of the experiments setup with an exemplary endoscopic image.

We showe in FIG. 14 the basic anatomy of a stomach and experimental setup from view of the endoscope.

Figure 15:
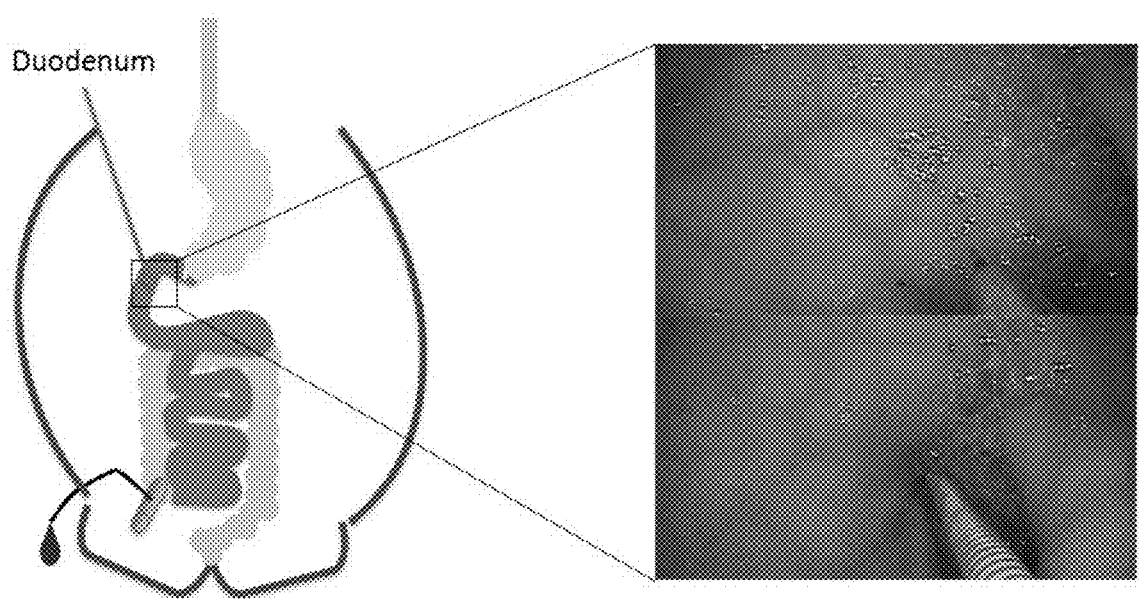
FIG. 15 shows a schematic of the experimental setup with two exemplary pictures of injection.

In order to demonstrate the feasibility of this technology we evaluated for the first time transgastric delivery of 10 units of rapid acting insulin (insulin aspart, NovoLog®). This was administered with the use of a Carr-Locke needle which is 500 μm in length and 514 μm in diameter. Frequent blood glucose monitoring was performed via the use of a central line (femoral venous catheter). In FIG. 15, we demonstrate 3 separate experiments demonstrating the hypoglycemic response to the insulin injection (red arrow marks the time of injection).

Figure 16:
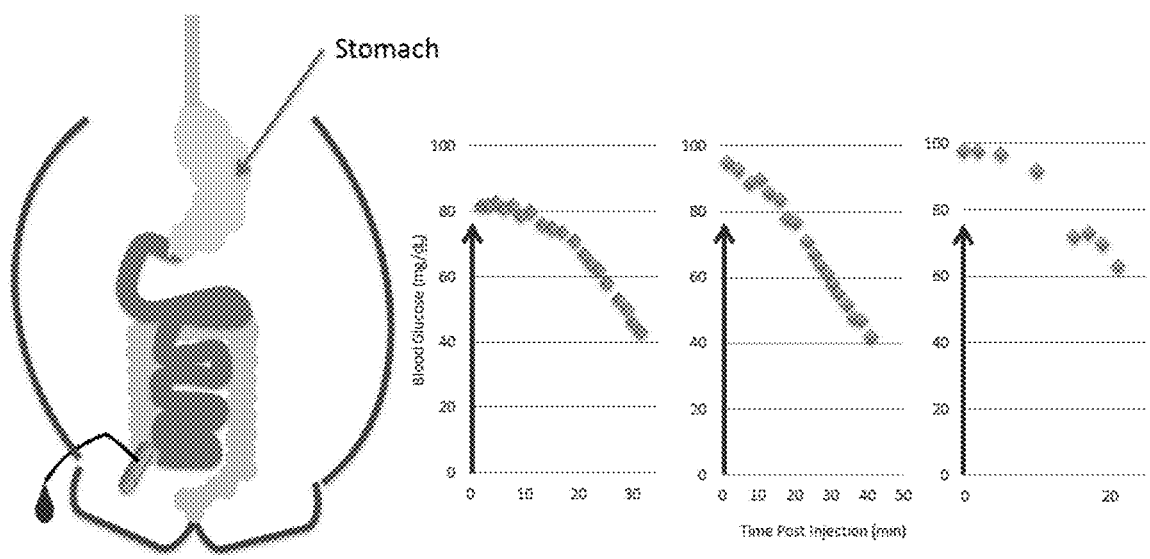
FIG. 16 include three plots of the blood glucose versus post-injection time in examples demonstrating the hypoglycemic response to the insulin injection in the stomach.

To further validate the delivery of biologics at different segment we further evaluated the use of microinjection in the duodenum (the first part of the small intestine). Here the pH ranges from 5.5-7 and there are a broader range of proteases. We evaluated the feasibility of this technology again utilizing insulin as a model biologic agent. The pictures in the right panel of FIG. 16 demonstrate the Carr-Locke needle in the upper panel and the needle in the duodenal tissue in the lower panel.

Figure 17:
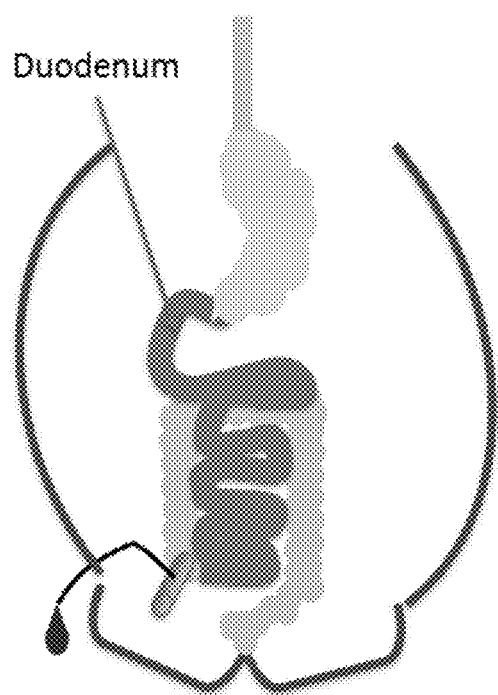
FIG. 17 include a plot of the blood glucose versus post-injection time in an example demonstrating the hypoglycemic response to the insulin injection in the duodenum.
Figure 17:
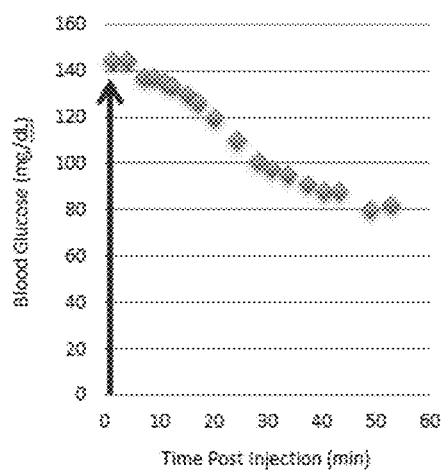

Similar to the transgastric delivery shown in FIG. 15, we showe in FIG. 17 the delivery of 10 units of rapid acting insulin (insulin aspart, NovoLog®). This was again administered with the use of the Carr-Locke needle. Frequent blood glucose monitoring was performed via the use of a central line (femoral venous catheter). Here we showed one experiment demonstrating the hypoglycemic response to the insulin injection (red arrow marks the time of injection).

Figure 18:
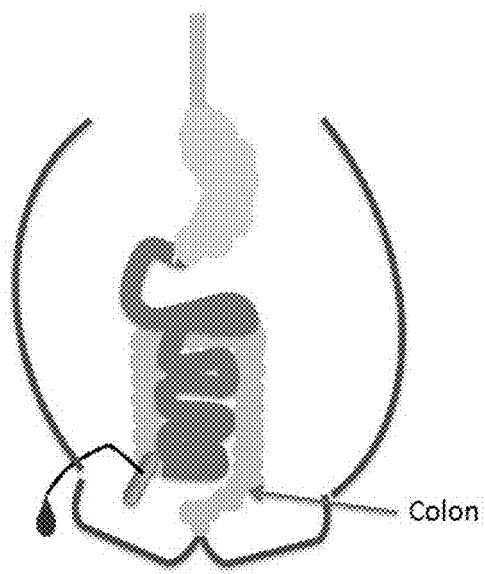
FIG. 18 shows a schematic of the experiments setup with two photographs of an exemplary device (prototype 3).
Figure 18:
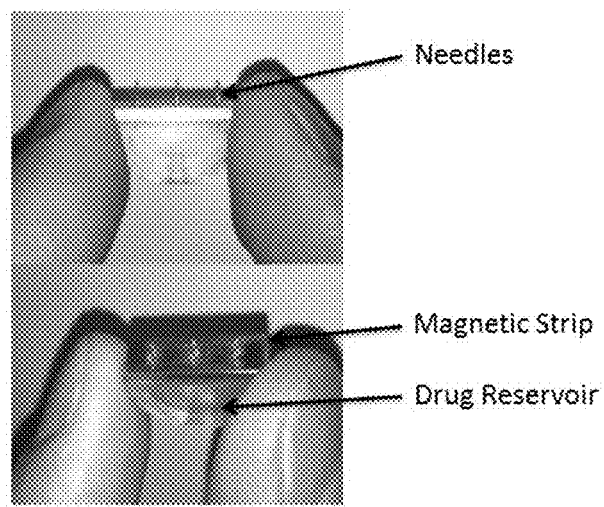

Having established that GIT delivery of insulin via microneedles is capable of inducing a hypoglycemic response we extended our studies to test our initial microneedle prototype, shown in FIG. 18. We first evaluated the prototype in the colon.

Figure 19:
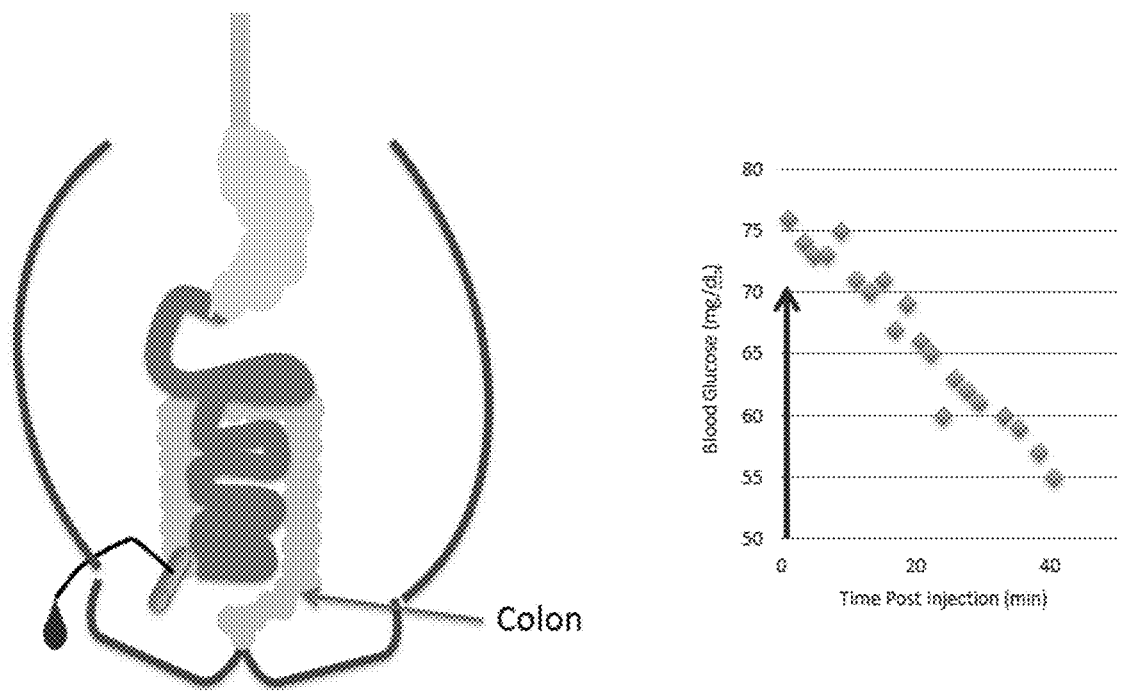
FIG. 19 shows a plot of the blood glucose versus post-injection time in an example demonstrating the hypoglycemic response to the insulin injection with the device shown in FIG. 18 (prototype 3).

We evaluated delivery in the colon with 20 units of rapid acting insulin (insulin aspart, NovoLog®). This was administered with the use of the microneedle prototype shown previously. Frequent blood glucose monitoring was performed via the use of a central line (femoral venous catheter). In FIG. 19, one experiment demonstrates the hypoglycemic response to the insulin injection with the prototype showed in FIG. 18 (red arrow marks the time of injection).

Insulin injections resulted in hypoglycemic responses in the animals within 20-40 minutes of administration. This was demonstrated in the stomach, duodenum. Conversely, insulin release without the use of needles did not induce a hypoglycemic (low glucose) response.

Example 5: Safety Experiments

In order to evaluate the safety of needles traversing through the gastrointestinal tract a prototype with needles 3-5 mm in length projecting circumferentially from a 1 cm (diameter)×2 cm (diameter) plastic capsule was constructed. The device was deployed with the aid of an endoscope in the stomach of a Yorkshire swine of 70 kg in weight. The animal was monitored with x-rays performed at least every 72 hrs and with serial clinical exams performed twice a day while the capsule remained in the animal's GI tract. X-rays were used to evaluate for the presence or absence of the device as well as for any evidence of gastrointestinal perforation (i.e. free air).

Following passage of the device the animal was euthanized within 48 hrs and all point of constriction in the gastrointestinal tract were isolated and examined.

Figure 20:
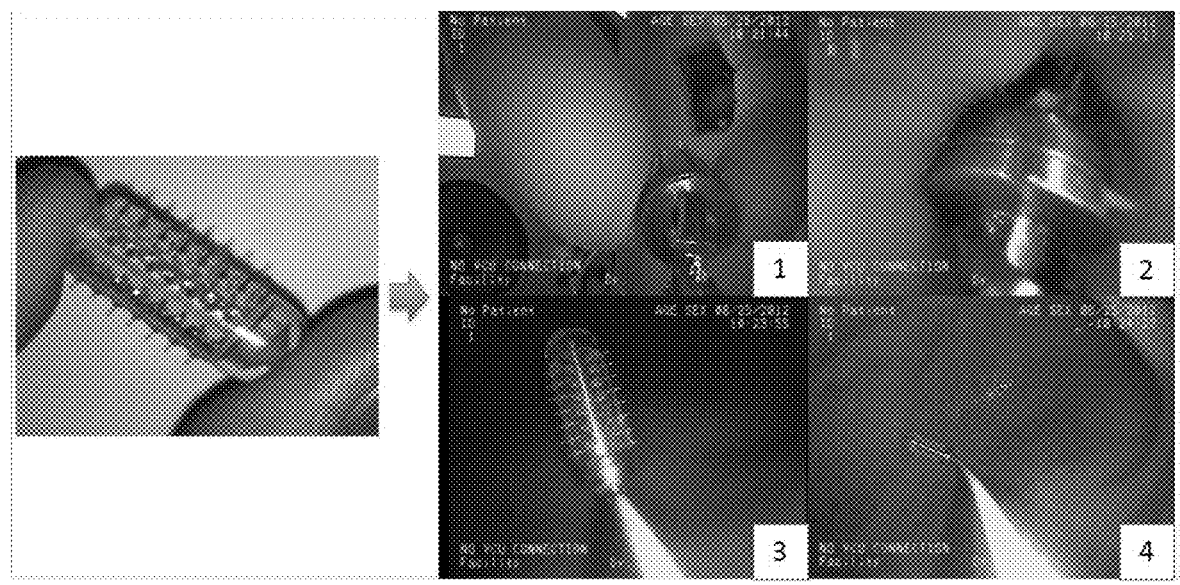
FIG. 20 shows photographs of an exemplary device and its delivery for safety experiments.

A prototype with microneedles arranged radially is shown on the left in FIG. 20. This was deployed endoscopically in the stomach of a pig (top right). The animal was monitored twice a day for any clincal signs of distress (e.g. anorexia, constipation, pain). Furthermore the animal was monitored with serial x-rays to document the presence of the capsule and its progress through the GIT. Within 48 hrs of passage the animal was euthanized and all points of constriction in the GIT were isolated. The animal remains asymptomatic throughout this evaluation.

Figure 21:
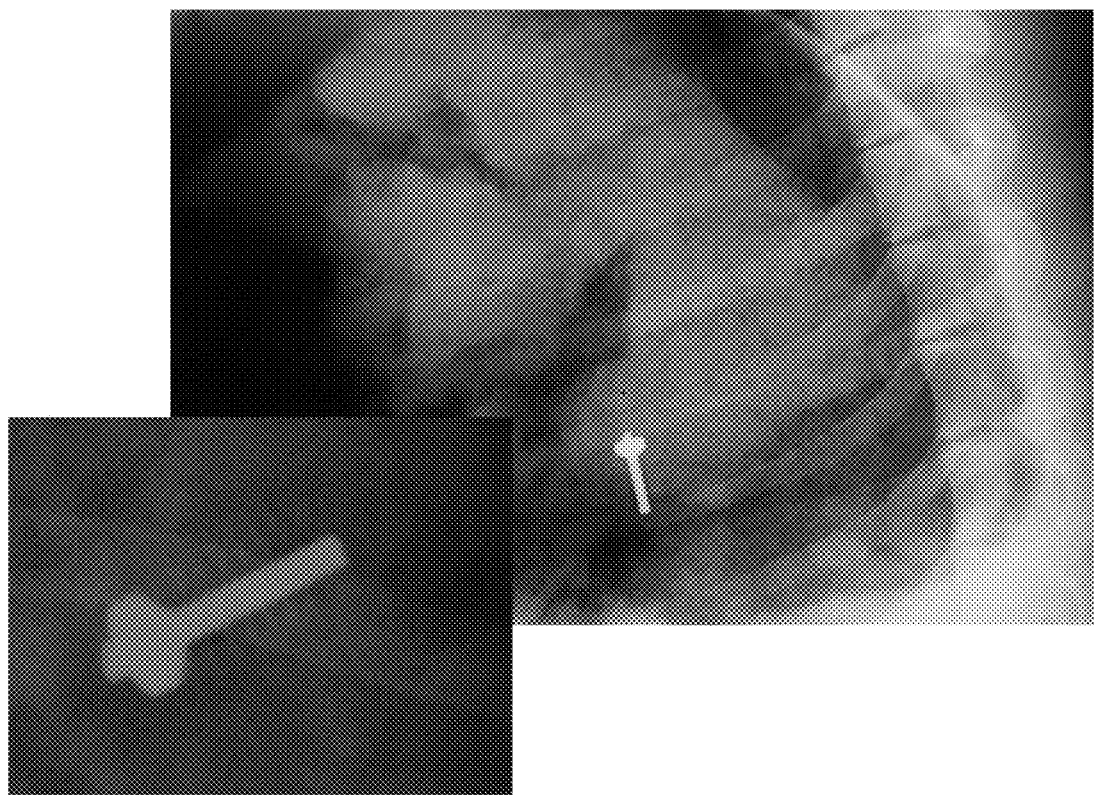
FIG. 21 shows radiographs of an exemplary device within the swine gastrointestinal tract.

In order to evaluate the safety of microneedle containing devices, a microneedle pill was placed in the stomach of a Yorkshire pig of approximately 70 kg and allowed to pass passively. In FIG. 21, we demonstrate an example of the microneedle prototype within the GI tract on a radiographs.

Figure 22:
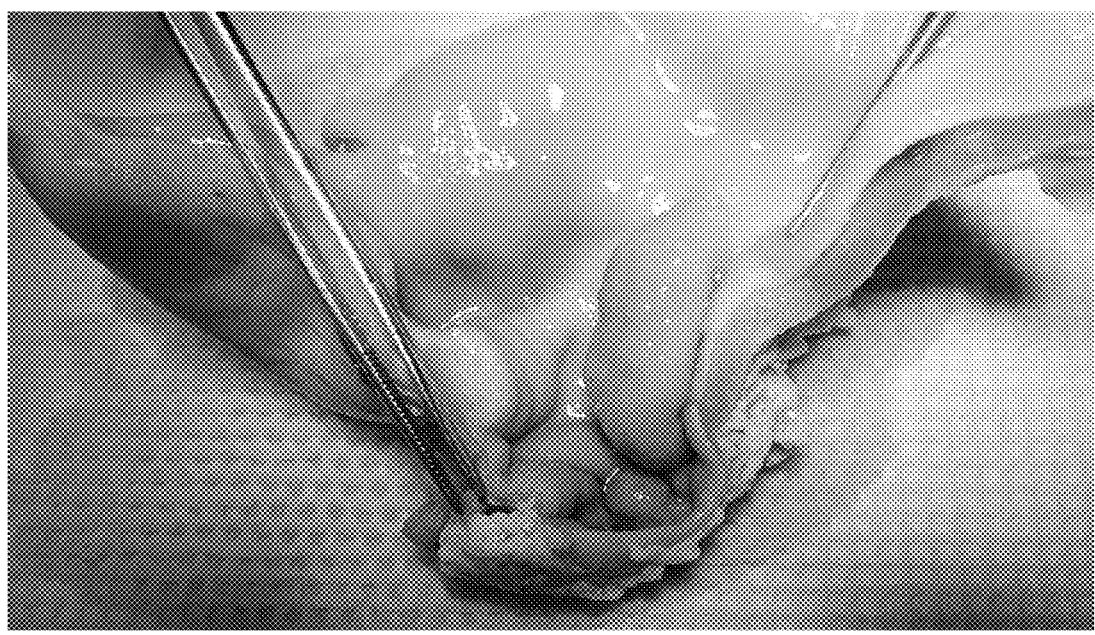
FIG. 22 illustrates macroscopic evaluation following passage of an exemplary device in pylorus.
Figure 23:
FIG. 23 illustrates macroscopic evaluation following passage of an exemplary device in the ileocecal valve and cecum.
Figure 24:
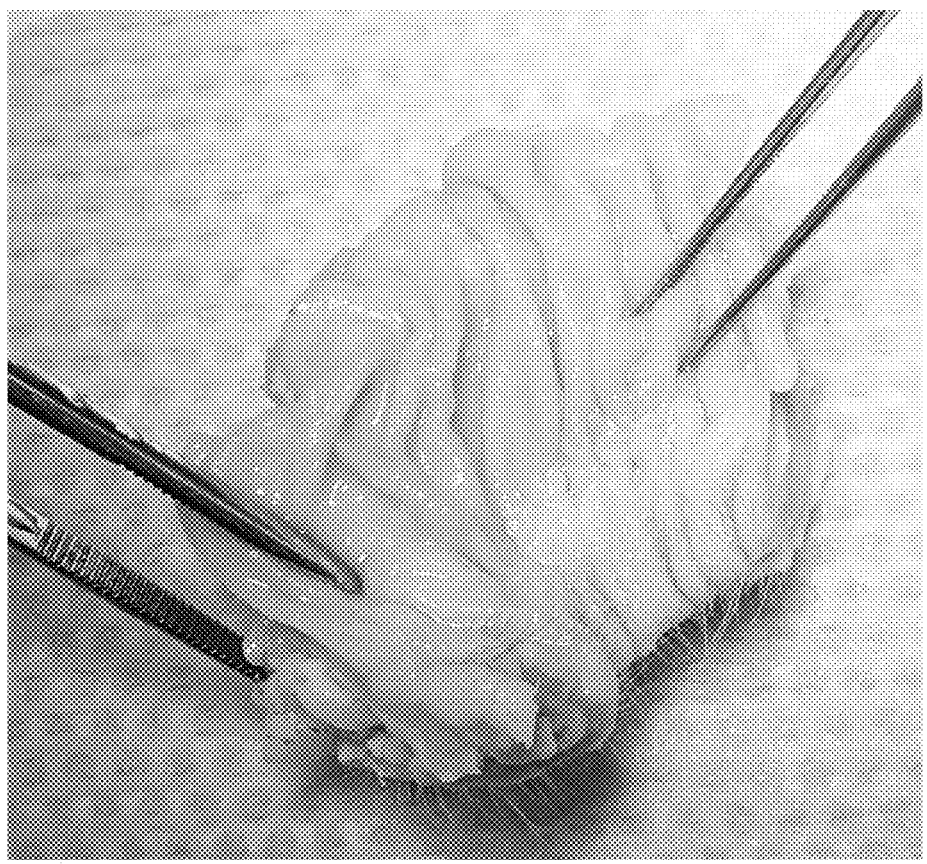
FIG. 24 illustrates macroscopic evaluation following passage of an exemplary device in the anal canal.

Forty-eight hours following the passage of a microneedle capsule a necropsy was performed and all points of constriction in the gastrointestinal tract were evaluated. Here we demonstrate the pylorus (FIG. 22), the ileocecal valve and cecum (FIG. 23), and the anal canal (FIG. 24) which as can be appreciated are intact (e.g., free of signs of injury).

Example 6: Abrasion Experiments

In order to evaluate the efficacy of abrasion and drug delivery a Yorkshire swine animal 70 kg in weight was fasted overnight. The animal was sedated and a central venous line was placed for frequent blood sampling. The rectum was cleansed with a tap water enema and an abrasion created in the rectal mucosa. A 10 ml enema with normal saline (0.9%) and 100 units of insulin aspart (Novolog®) was instilled in the rectum and frequent glucose measurement performed. As a control for abrasion a 10 ml enema with normal saline (0.9%) and 100 units of insulin aspart (Novolog®) was instilled in the rectum of an animal without an abrasion and frequent glucose measurement performed.

A decrement in serum glucose levels was noted from a baseline glucose of 80-82 mg/dL to 60 mg/dL within 20-30 minutes of administration of the insulin enema. Glucose levels did not decrease in the absence of an abrasion.

Other Embodiments and Equivalents

Although this disclosure has described and illustrated by reference to certain embodiments and examples, it is to be understood that the disclosure is not restricted to those particular embodiments or examples. Rather, the disclosure includes all embodiments that are functional and/or equivalents of the specific embodiments and examples that have been described.

We claim:

1. A device, comprising:
a payload and a single microneedle protruding from the device's surface, wherein the device, including the single protruding, microneedle, is dimensioned and constructed so that, when orally administered to a subject, the device, including the single protruding microneedle, enters the oral cavity, and passively travels through the subject's gastrointestinal tract until the device, including the protruding microneedle, is excreted from the subject and, during the passive travel, the single protruding microneedle interacts with internal tissue of the gastrointestinal tract and delivers the payload thereto, or through a wall of a vessel associated therewith,
wherein the dimensions and construction of the protruding microneedle include:
a length appropriate to penetrate or abrade a mucus and/or one or more mucosal layers, which length is within a range of less than about 5.0 mm and more than about 1.0 mm, and
wherein the payload is delivered to a target site selected from the group consisting of esophagus, stomach, small intestine, and large intestine.

2. The device of claim 1, wherein the internal tissue is a part of a vessel wall.

3. The device of claim 1, wherein the device has a lumen bounded by a wall.

4. The device of claim 1, wherein a portion of the device comprises a magnetic material.

5. The device of claim 1, further comprising a coating.

6. The device of claim 5, wherein the coating is selected from a group consisting of a pH-sensitive coating, an inflammatory-sensitive coating, a virus/bacteria-sensitive coating, a cancer specific coating, a hydrolytically degradable coating, a medicated coating, an inert coating and any combination thereof.

7. The device of claim 6, arranged and constructed to transition from an initial state to an exposed state that differ from one another in the extent to which the coating is present on the microneedle.

8. The device of claim 1, wherein at least one dimension or the greatest dimension of the device is within a range of about 0.1 cm to about 5 cm, 0.1 μm to about 100 μm, about 100 μm to about 1 cm, or about 1 cm to about 10 cm.

9. The device of claim 1, wherein the device transitions from an inactivated phase to an activated phase in response to a trigger so that the device in the activated phase delivers the payload to the internal tissue or the vessel wall.

10. The device of claim 9, wherein the trigger is selected from the group consisting of presence of blood, specific molecules/entities, magnetic fields, ultrasound, electric fields, pH, enzymatic activity, temperature, light, mechanical forces and any combination thereof.

11. The device of claim 1, wherein the payload is or comprises an agent selected from the group consisting of a therapeutic agent, a prophylactic agent, a nutraceutical agent, a diagnostic agent or any combination thereof.

12. The device of claim 1, wherein the dimensions and construction of the microneedle include a shape selected from the group consisting of a rectangle, a cone, a pyramid, a cylinder, and a tube.

13. The device of claim 8, wherein the at least one dimension or the greatest dimension of the device is within a range of about 1 cm to 2 cm.

14. The device of claim 13, wherein the at least one dimension of the device comprises the length or diameter of the device, not including the length of the protruding microneedle.

15. A method of delivering at least one payload to an internal gastrointestinal tissue of a subject, or through a wall of a vessel associated therewith, the method comprising steps of:
providing a device dimensioned and constructed for oral administration, wherein the device includes a plurality of microneedles protruding from the device surface, and a payload;
orally administering the device to a subject so that the device, including the plurality of protruding microneedles, enters the oral cavity and passively travels through the subject's gastrointestinal tract until the device, including the plurality of protruding microneedles, is excreted, wherein, during the passive travel, one or more protruding microneedles of the plurality of protruding microneedles interact with internal tissue of the gastrointestinal tract, so that the payload is delivered to the internal tissue, or through a wall of a vessel associated therewith,
wherein the dimensions and construction of each protruding microneedle of the plurality of protruding microneedles include:
a length appropriate to penetrate or abrade a mucus and/or one or more mucosal layers, which length is within a range of less than about 5.0 mm and more than about 1.0 mm, and wherein the payload is delivered to a target site selected from the group consisting of esophagus, stomach, small intestine, and large intestine.

16. The method of claim 15, wherein one or more microneedles of the plurality of microneedles are hollow.

17. The method of claim 16, wherein at least one of the one or more hollow microneedles of the plurality of microneedles is cannulated, defining a channel that enables storage or introduction of the at least one payload.

18. The method of claim 15, wherein one or more microneedles of the plurality of microneedles protrude substantially radially.

19. The method of claim 15, wherein the range is less than about 5 mm and more than about 2 mm.

20. The method of claim 15, wherein each microneedle of the plurality of microneedles has a gauge and/or an outer diameter within a range of about 1 µm to about 50 µm, about 50 µm to about 200 µm, about 200 µm to about 500 µm, about 500 µm to about 1000 µm, about 1 mm to about 5 mm or about 600 µm to about 10 µm.

21. The method of claim 15, wherein one or more of the microneedles of the plurality of microneedles are solid.

22. The method of claim 15, wherein the dimension and construction of each microneedle of the plurality of microneedles include a shape selected from the group consisting of a rectangle, a sphere, a cone, a pyramid, a cylinder, and a tube.

* * * * *